(12) United States Patent
Sekine et al.

(10) Patent No.: US 10,259,578 B2
(45) Date of Patent: Apr. 16, 2019

(54) UNMANNED AERIAL VEHICLE, RELIEF SYSTEM, AND RELIEF METHOD

(71) Applicant: TERUMO KABUSHIKI KAISHA, Tokyo (JP)

(72) Inventors: Yuusuke Sekine, Kanagawa (JP); Shinya Sano, Kanagawa (JP); Chisato Iwakiri, Kanagawa (JP); Ryouta Yamane, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 96 days.

(21) Appl. No.: 15/607,074

(22) Filed: May 26, 2017

(65) Prior Publication Data

US 2017/0341745 A1 Nov. 30, 2017

(30) Foreign Application Priority Data

May 30, 2016 (JP) ................................ 2016-107764

(51) Int. Cl.
| | |
|---|---|
| *B64C 39/02* | (2006.01) |
| *A61N 1/39* | (2006.01) |
| *B64D 1/08* | (2006.01) |
| *G05D 1/00* | (2006.01) |
| *G05D 1/10* | (2006.01) |
| *G06F 19/00* | (2018.01) |

(52) U.S. Cl.
CPC ............... *B64C 39/02* (2013.01); *A61N 1/39* (2013.01); *B64D 1/08* (2013.01); *G05D 1/0088* (2013.01); *G05D 1/102* (2013.01); *G06F 19/34* (2013.01)

(58) Field of Classification Search
CPC ..................................................... B64C 39/02
See application file for complete search history.

(56) References Cited

U.S. PATENT DOCUMENTS

| | | | | |
|---|---|---|---|---|
| 9,422,139 | B1* | 8/2016 | Bialkowski | ........... B64C 39/024 |
| 2015/0148988 | A1* | 5/2015 | Fleck | ................... G05D 1/0011 |
| | | | | 701/2 |
| 2017/0166309 | A1* | 6/2017 | Sekiya | ................. B64D 11/062 |

FOREIGN PATENT DOCUMENTS

| | | |
|---|---|---|
| JP | 2015-184350 | 10/2015 |
| JP | 2015-195030 | 11/2015 |

* cited by examiner

*Primary Examiner* — Michael D Lang
(74) *Attorney, Agent, or Firm* — Jason H. Vick; Sheridan Ross, PC

(57) ABSTRACT

Provided are an unmanned aerial vehicle executing relief work in an emergency such as a disaster, a relief system, and a relief method for performing relief work by using an unmanned aerial vehicle. An unmanned aerial vehicle capable of performing autonomous flight includes a receiving unit receiving an input of relief work from a user A2 and a control unit controlling the execution of the relief work based on content of the input received by the receiving unit.

20 Claims, 14 Drawing Sheets

100

100

121a

10

UNMANNED AERIAL VEHICLE, RELIEF SYSTEM, AND RELIEF METHOD

CROSS REFERENCE TO RELATED APPLICATIONS

The present application claims the benefit of and priority, under 35 U.S.C. § 119(e), to Japanese Application No. 2016-107764, filed May 30, 2016, entitled "UNMANNED AERIAL VEHICLE, RELIEF SYSTEM AND RESCUE METHOD," the entire disclosure of which is incorporated herein by reference in its entirety for all that it teaches and for all purposes.

TECHNICAL FIELD

The present invention generally relates to an unmanned aerial vehicle, a relief system, and a relief method.

BACKGROUND

Much attention has been paid in various industrial fields these days to the use of unmanned aerial vehicles, capable of performing autonomous flight and called drones, and the like. For example, attempts have been made to improve advertising effects by devising movement control for unmanned aerial vehicles equipped with digital signage (electronic signboards) and to use unmanned aerial vehicles as means for transporting supplies (refer to Japanese Patent Application No. JP-A-2015-184350 and Japanese Patent Application No. JP-A-2015-195030).

SUMMARY

Problems to Solve

Problems emerging at disaster sites, by the way, include relief for victims in need of urgent medical treatment due to cardiopulmonary arrest and so on and relief for people in need of assistance such as inpatients and senior citizens.

Victims to cardiopulmonary arrest and so on must be urgently treated by the use of cardiopulmonary resuscitation (CPR) based on an automated external defibrillator (AED), cardiac massage, and the like. In actuality, however, automated external defibrillators that can be immediately used are nearby and rescuers to perform the emergency treatment are around the victims in few cases at disaster sites. Even if there are people around the victims, most of them are likely to be victims themselves and in no position to provide relief for the others. Besides, the progress of automated external defibrillator installation has been slower in provincial cities than in major cities.

In the event of a fire attributable to an earthquake and the like, a lot of people fail to escape from the fire and then loss of precious lives follows. Those in need of assistance such as inpatients in hospitals and home care patients undergoing home medical care, in particular, include a lot of bedridden patients and patients with restricted mobility, and they are likely to be confined in their residences or buildings and fall victim to the disaster.

The embodiments herein address the problems at disaster sites by providing an unmanned aerial vehicle that is capable of performing autonomous flight.

An object of the embodiments of the present disclosure is to provide an unmanned aerial vehicle executing relief work in an emergency such as a disaster, a relief system, and a relief method for performing relief work by using an unmanned aerial vehicle.

Solution to Problems

An unmanned aerial vehicle according to the embodiments of the present disclosure, which is an unmanned aerial vehicle capable of performing autonomous flight, includes a receiving unit receiving an input of relief work from a user and a control unit controlling execution of the relief work based on content of the input received by the receiving unit.

A relief method according to the embodiments of the present disclosure, which is a relief method for performing relief work by using an unmanned aerial vehicle capable of performing autonomous flight, includes a receiving step of receiving processing content from a user via a receiving unit of the unmanned aerial vehicle and a control step of controlling the execution of the relief work following the processing content by using a control unit of the unmanned aerial vehicle.

Advantageous Effects

According to the unmanned aerial vehicle or the relief method described above, the relief work following the processing content designated by the user is executed at a disaster site in an emergency. The unmanned aerial vehicle is capable of moving in the air, and thus is capable of quickly moving in the shortest path to the disaster site regardless of the traffic situation around the disaster site. Accordingly, appropriate relief work can be quickly executed with respect to a relief recipient in need of emergency relief from, for example, a state of cardiopulmonary arrest.

DETAILED DESCRIPTION

Figure 1A:
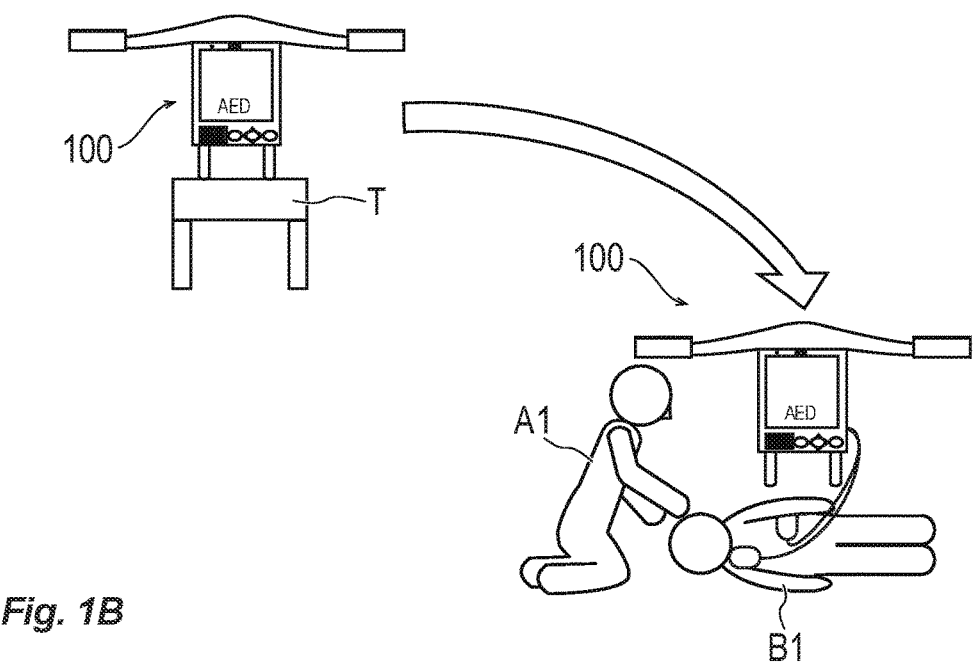
FIGS. 1A and 1B are conceptual diagrams for showing a normal mode of an unmanned aerial vehicle and a relief system according to embodiments of the present disclosure.

Hereinafter, embodiments of the present invention will be described with reference to accompanying drawings. Note that, the following description does not limit the technical scope of and the significance of terms in the scope of claims. Dimension ratios in the drawings are exaggerated for convenience of description and differ from actual ratios in some cases.

An overview of a relief system 1 according to according to embodiments of the present disclosure will be described first. FIGS. 1 and 2 are conceptual diagrams illustrating the relief system 1.

The relief system 1 has an unmanned aerial vehicle 100 capable of performing autonomous flight, an information terminal device 200 transmitting a transmission command to the unmanned aerial vehicle 100, and a management server 300 performing data transmission and reception to and from the unmanned aerial vehicle 100 and the information terminal device 200.

The unmanned aerial vehicle 100 is a flying device flying in the air and moving to a desired destination. The unmanned aerial vehicle 100 has a calculation processing function based on a central processing unit (CPU) and a function to perform wireless communication with the information terminal device 200 and the management server 300 via, for example, a base station (not illustrated).

Figure 1B:
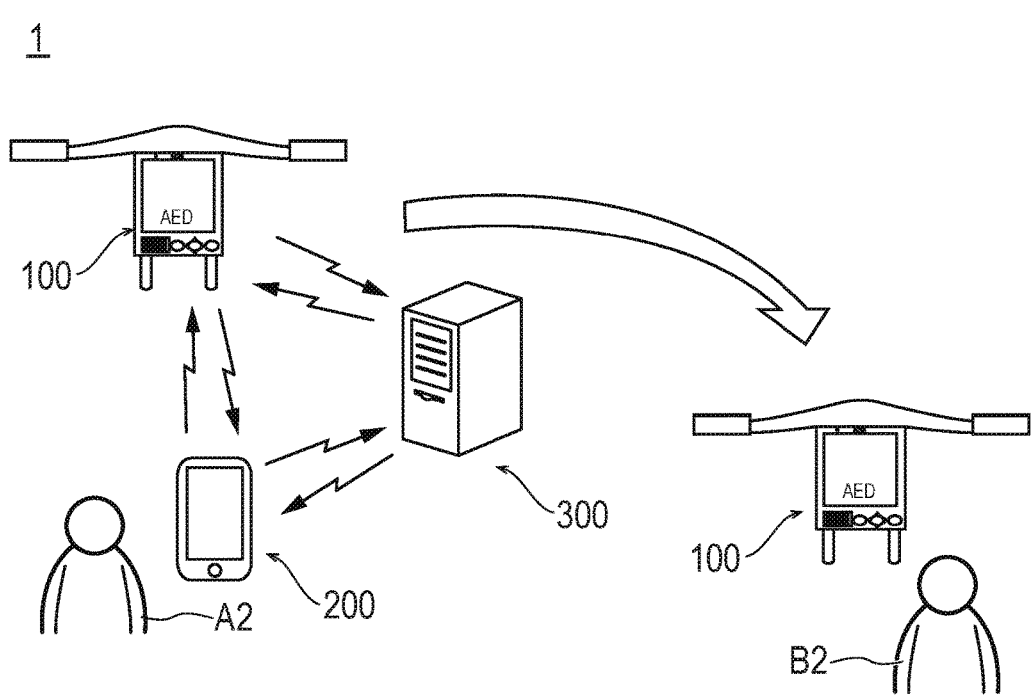
Figure 2:
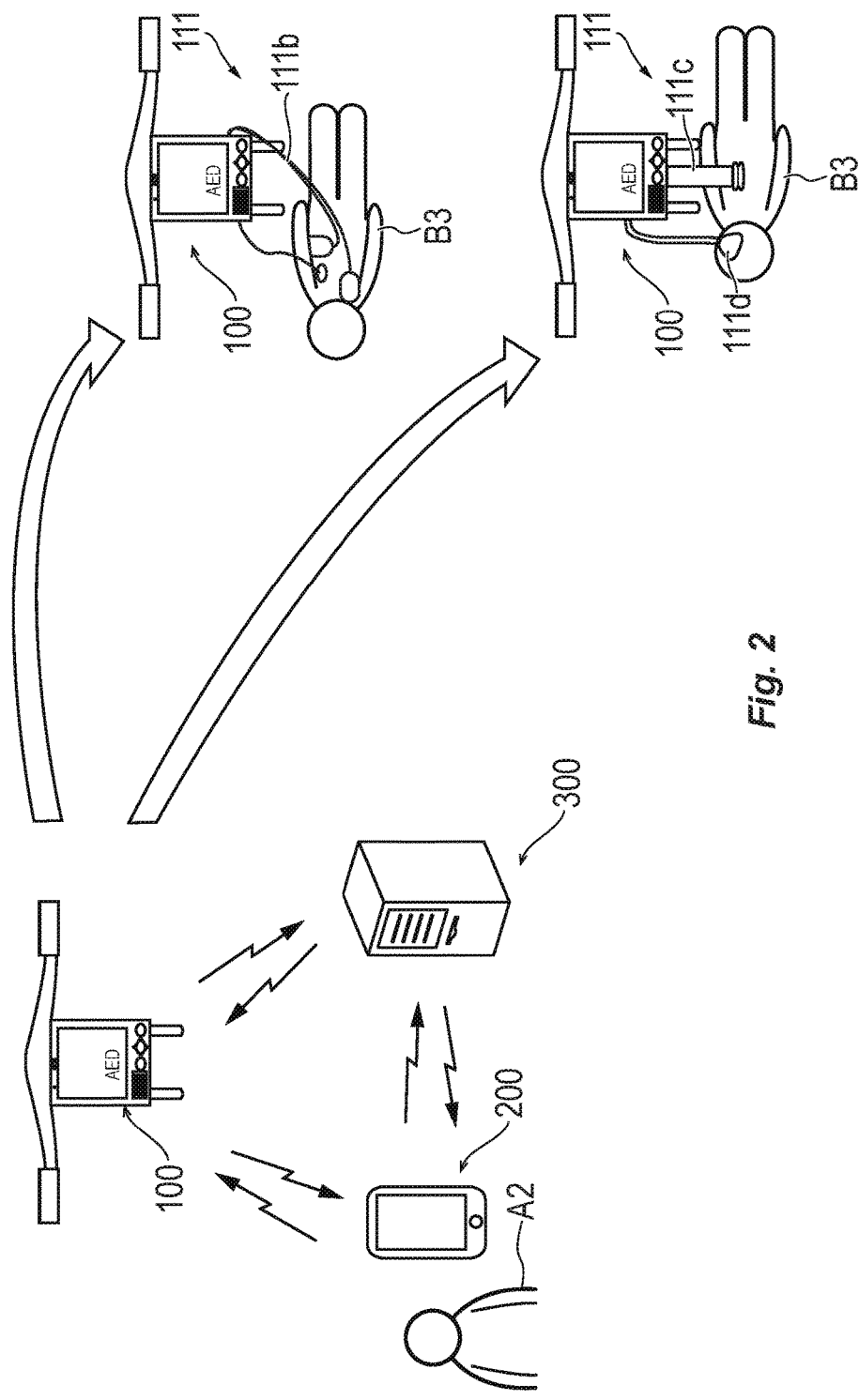
FIG. 2 is a conceptual diagram for showing an emergency mode of the unmanned aerial vehicle and the relief system according to embodiments of the present disclosure.

The unmanned aerial vehicle 100 is configured to be capable of selectively switching between a normally used normal mode, which is illustrated in FIGS. 1A and 1B, and an emergency mode, which is illustrated in FIG. 2 and used in an emergency such as disaster occurrence.

In the normal mode, the unmanned aerial vehicle 100 is in a standby state as illustrated in FIG. 1A or is in an operating state as illustrated in FIG. 1B. In the standby state, the unmanned aerial vehicle 100 stands by on an installation stand T where the unmanned aerial vehicle 100 is capable of taking off and landing. In the operating state, the unmanned aerial vehicle 100 executes medical support work (task support work) at a medical site such as a hospital.

As illustrated in FIG. 1A, the unmanned aerial vehicle 100, in the standby state of the normal mode, stands by at unmanned aerial vehicle's installation place such that the unmanned aerial vehicle 100 can be used as medical equipment such as an automated external defibrillator (AED) so that a rescuer A1 can provide emergency treatment for an acute patient B1, if necessary. Note that, the place where the unmanned aerial vehicle 100 is installed is not limited to the hospital and may be a fire station, a train station, a public facility, etc.

As illustrated in FIG. 1B, the unmanned aerial vehicle 100, in the operating state of the normal mode, executes the medical support work to assist in work supposed to be performed by a user A2, who is a health care worker in the hospital, or to replace the user A2. The unmanned aerial vehicle 100 receives an input of the medical support work designated by the user A2 through the information terminal device 200. Once the input of the medical support work is received, the unmanned aerial vehicle 100 performs various types of work related to medical work in cooperation with another person (such as another health care worker) B2 or provides a medical service for another person (such as an inpatient) B2. Note that, details of the medical support work executed by the unmanned aerial vehicle 100 will be described later.

In the emergency mode, the unmanned aerial vehicle 100 moves to a disaster site and executes relief work as illustrated in FIG. 2. The "relief work" means protection, nursing, or treatment performed for a relief recipient. The "protection" includes, for example, evacuation support for a victim (relief recipient) B3. The "nursing" includes, for example, support for the everyday life of the victim B3 in a shelter and hygiene management. The "treatment" includes, for example, diagnosis based on bioinformation acquisition, an interview, or the like, injury and disease handling, and emergency injury and disease treatment. Herein, the "treatment," with respect to the victim B3, will be described as a main example of the "relief work" but is not so limited.

Upon receiving the selection of the emergency mode, the unmanned aerial vehicle 100 switches from the normal mode to the emergency mode and receives an input of the relief work designated by the user A2 through the information terminal device 200. Upon receiving the input of the relief work, the unmanned aerial vehicle 100 moves to the disaster site and executes the relief work with respect to the victim B3. Note that, the "disaster" is not limited to a natural disaster such as an earthquake and may also include disasters resulting from human factors such as a fire. Details of the relief work executed by the unmanned aerial vehicle 100 will be described later.

The information terminal device 200 is a terminal device carried around by the user A2. For example, the information terminal device 200 can be made up of a portable terminal device that has a calculation processing function based on a CPU (e.g., a smartphone, a portable communication device that does not have a call function, or the like).

The information terminal device 200 is equipped with a function to perform the wireless communication with the unmanned aerial vehicle 100 and the management server 300 via, for example, the base station (not illustrated), a function to execute an application started when the medical support work or the relief work by the unmanned aerial vehicle 100 is executed, an imaging function to capture a still image and/or a moving image, and/or a GPS function to detect a position of the information terminal device 200.

Examples of communication methods of the unmanned aerial vehicle 100 and the information terminal device 200 include code-division multiple access (CDMA), frequency division multiple access (FDMA), time division multiple access (TDMA), wideband-CDMA (W-CDMA), and a personal handyphone system (PHS). In addition, the unmanned aerial vehicle 100 and the information terminal device 200 can be provided with a function corresponding to a method of communication by an internet protocol (IP) packet in compliance with wireless local area network (WLAN) standards as a wireless interface.

The management server 300 is a server device managing the entire system and performs, for example, management of the unmanned aerial vehicle 100, management of the user using the unmanned aerial vehicle 100, and/or data collection management.

The management server 300 is connected to the unmanned aerial vehicle 100 and the information terminal device 200 via a wireless communication network. The management server 300 includes a function as a web server, performs transmission and reception of, for example, hypertext markup language (HTML) data, image data, voice data, audio data, and/or music data, and performs accumulation of each of the data by using a known system such as the World Wide Web (WWW). Each of the data can be delivered from the management server 300 to the unmanned aerial vehicle 100 in response to a request through the application executed on the information terminal device 200.

The data transmission and reception between the unmanned aerial vehicle 100 and the management server 300 and the data transmission and reception between the information terminal device 200 and the management server 300 may be also performed through a communication network connected via a predetermined relay device (such as a modem, a terminal adapter, and a gateway device). A distributed communication network established in a building such as a hospital and a public facility selected as a place where the management server 300 is installed, for example, can be used as this communication network. The distributed communication network can be established by, for example, various communication lines (such as a dedicated line and a public line like telephone, Integrated Services Digital Network (ISDN), Asymmetric digital subscriber line (ADSL), and optical lines) being connected to each other by communication protocol Transmission Control Protocol/Internet Protocol (TCP/IP) being used.

Figure 3A:
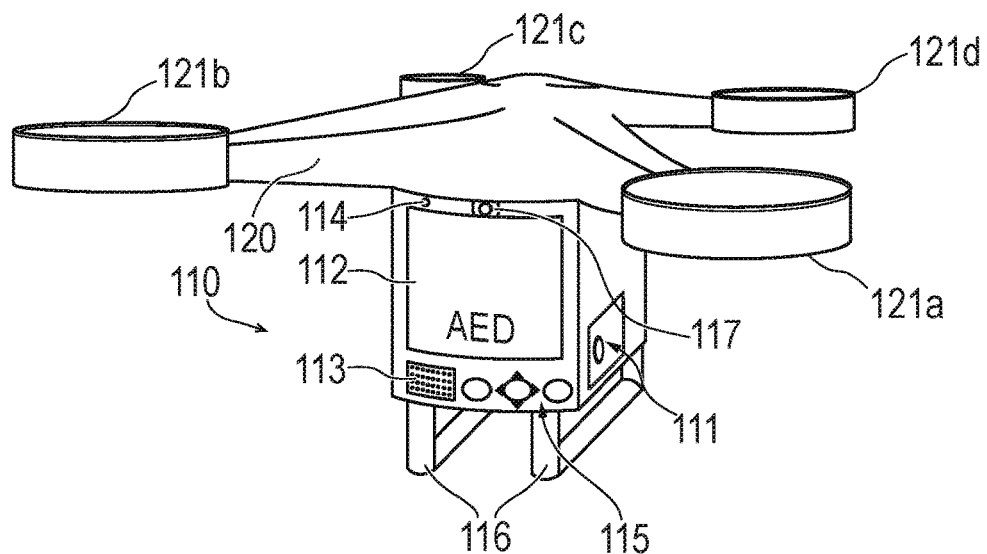
FIG. 3A is a perspective view of the unmanned aerial vehicle according to embodiments of the present disclosure.

Hereinafter, configuration of each portion of the unmanned aerial vehicle 100 will be described with reference to FIG. 3. FIG. 3A is a perspective view of the unmanned aerial vehicle 100 and FIG. 3B is a front view of the unmanned aerial vehicle 100.

Figure 3B:
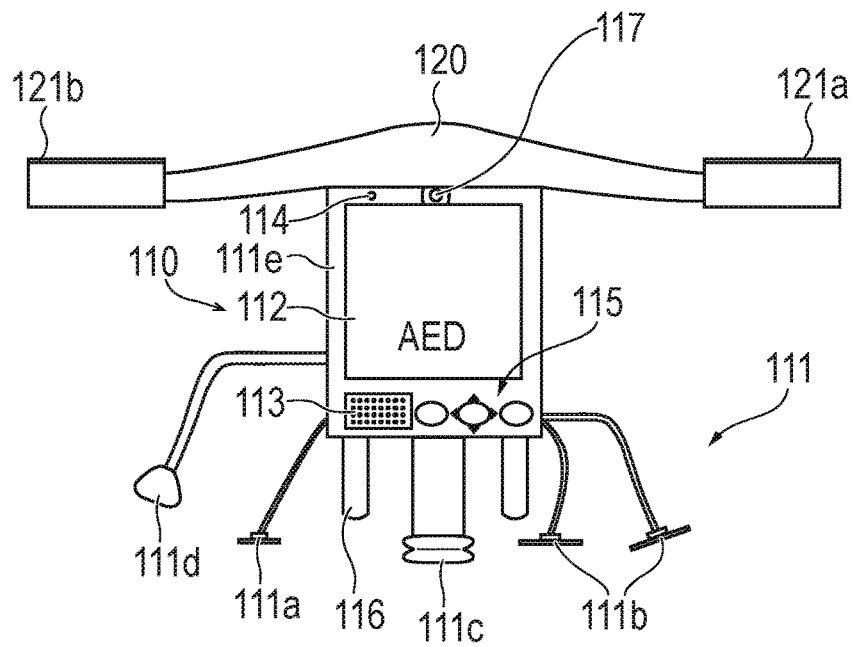
FIG. 3B is a front view of the unmanned aerial vehicle according to embodiments of the present disclosure.

As illustrated in FIGS. 3A and 3B, the unmanned aerial vehicle 100 has a main body portion 110, an upper housing 120 attached to the main body portion 110, and lift generating units 121a to 121d disposed on the upper housing 120. The unmanned aerial vehicle 100 has no rotary blade and is capable of flying in the air by using lift generated by an air flow formed by the lift generating units 121a to 121d.

The main body portion 110 has a treatment unit 111 conducting medical treatment with respect to the victim B3, a display unit 112 capable of displaying an image, a speaker (voice output unit) 113 capable of outputting sounds including voice and music, a microphone (voice input unit) 114 allowing an input of sounds including voice and music, various operation buttons 115 operated during adjustment of, for example, switching of content of the display on the display unit 112 and the volumes of the speaker 113 and the microphone 114, a load receiving unit 116 for holding an article or the like as a transport object, and an imaging unit 117 capable of capturing still and moving images.

The treatment unit 111 has medical equipment 111a to 111d and a housing 111e accommodating the medical equipment 111a to 111d. The medical equipment 111a to 111d consist of a bioinformation measuring instrument 111a, an automated external defibrillator (AED) 111b, an automatic cardiac massager 111c, and an artificial respirator 111d. In a case where the medical equipment 111a to 111d are not used, the medical equipment 111a to 111d are stored in the housing 111e (refer to FIG. 3A). The medical equipment 111a to 111d are configured to be retrievable to the outside by the user such as the rescuer A1 or a drive unit 150 (described later) when the medical equipment 111a to 111d are used (refer to FIG. 3B).

The bioinformation measuring instrument 111a is provided with an electrode pad, a sphygmomanometer, and the like and acquires data by measuring bioinformation on the acute patient B1 and the victim B3 such as their electrocardiograms, heart rates, blood pressures, and body temperatures. The configuration of the bioinformation measuring instrument 111a is not particularly limited insofar as bioinformation measuring instrument 111a is capable of performing bioinformation measurement. The bioinformation measuring instrument 111a can be configured to be capable of measuring the bioinformation from the neck, fingertip, or the like of the victim B3 that is exposed to the outside in a case where, for example, he or she is buried under rubble.

The automated external defibrillator 111b is provided with an electrode pad and the like and performs emergency treatment for recovering the function of the heart of the acute patient B1 or the victim B3 with cardiopulmonary failure. Specifically, the automated external defibrillator 111b performs the treatment for recovering the function of the heart by applying an electric shock to the heart by cardioversion in a state where the electrode pad is in contact with the chest of the acute patient B1 or the victim B3. Note that, in a case where clothes or the like hinder the direct contact between the electrode pad and the chest of the acute patient B1 or the victim B3, the clothes need to be taken off or torn apart. In this regard, the unmanned aerial vehicle 100 can be provided with a tearing function of a cutter, scissors, or the like and a gripping tool for removing clothes. The unmanned aerial vehicle 100 has a sensor for sensing whether the acute patient B1 or the victim B3 has a metal impalement because the acute patient B1 or the victim B3 has metal impalements in some cases. The unmanned aerial vehicle 100 may be provided with means for removing the metal from his or her body in a case where he or she has a metal impalement. By having these configurations, the unmanned aerial vehicle 100 is capable of realizing a highly safe emergency treatment even if there is no one around.

The automatic cardiac massager 111c and the artificial respirator 111d perform treatment for cardiopulmonary resuscitation (CPR). Specifically, the automatic cardiac massager 111c is provided with a compressing unit compressing the chest of the acute patient B1 or the victim B3 and performs cardiac massage by repeating the compression and release of the compression of the chest of the acute patient B1 or the victim B3 at predetermined intervals. Note that, the automatic cardiac massager 111c may be provided by affixing a belt to the acute patient B1 or the victim B3 as well. The artificial respirator 111d performs artificial respiration for respiratory assistance by sending gas into the lungs of the acute patient B1 or the victim B3.

The display unit 112 can be made up of a liquid crystal display. The display unit 112 can be made up of a capacitive touch panel or the like as well. The speaker 113 and the microphone 114 can be made up of, for example, a known acoustic speaker and a known capacitor microphone used for voice and music and/or audio output and input. The imaging unit 117 can be made up of, for example, known digital still and video cameras used for still and moving image capturing.

Figure 4A:
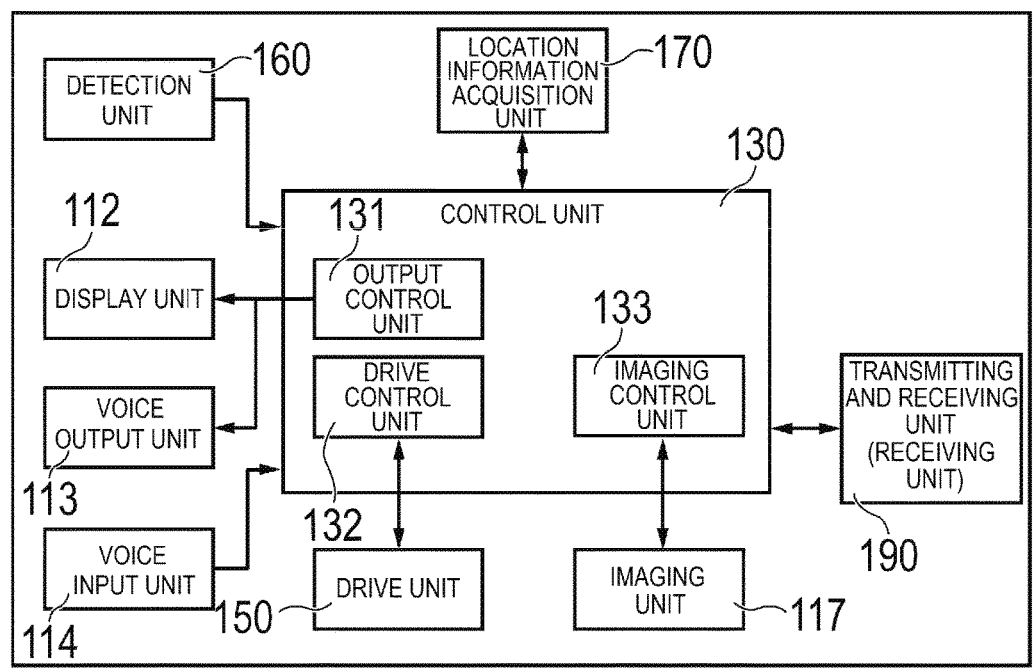
FIG. 4A is a block diagram schematically illustrating an internal structure of the unmanned aerial vehicle according to the embodiment and FIG. 4B is a block diagram schematically illustrating an internal structure of an information terminal device according to embodiments of the present disclosure.

Also disposed in the main body portion 110 are the drive unit 150, a detection unit 160, a location information acquisition unit 170, and a transmitting and receiving unit 190 (refer to FIG. 4A).

The drive unit 150 can be a device for giving a drive force to the treatment unit 111 and each of the lift generating units 121a to 121d. The drive unit 150 can be made up of, for example, a robot arm, an impeller, an electric motor, a drive actuator, and/or a power source.

The detection unit 160 functions to discover the victim B3 in need of relief at the disaster site and acquire various types of information such as the altitude, velocity, and direction of movement of the unmanned aerial vehicle 100 and unmanned aerial vehicle's distance from an obstacle. An appropriate combination of, for example, an acceleration sensor, a gyro sensor, a magnetic sensor, and a radar sensor sensing persons and obstacles can constitute the detection unit 160.

The location information acquisition unit 170 is a module acquiring a current location of the unmanned aerial vehicle 100. The location information acquisition unit 170 is provided with, for example, a GPS function and a function to determine the current location from information such as the intensity of a signal from a radio base station.

When a predetermined building is approached during the flight, the unmanned aerial vehicle 100 provides notification to that effect based on the information acquired by the location information acquisition unit 170. The unmanned aerial vehicle 100 has not only the notification function but also a "building avoidance function", which is to make impossible the flight along a route approaching the building or perform route selection so that the flight is performed via a bypass route. Alarm notification performed through the display unit 112, the speaker 113, or the like can be adopted as a method for the notification. The operation control for making the flight impossible and the bypass route selection can be incorporated in advance as a type of operation processing in an operation program executed by a control unit 130. Note that, examples of the facility described above include facilities of importance such as the official residence of the Prime Minister of Japan, its central ministries, and a nuclear power plant in a case where Japan is home to the facility. The unmanned aerial vehicle 100 is configured to execute the building avoidance function in a case where, for example, unmanned aerial vehicle 100 trespasses on a predetermined range around the facility described above (such as a range of 300 m to 1,000 m and a range of 300 m in particular).

The transmitting and receiving unit 190 performs wireless data communication via a wireless communication network. In addition, the transmitting and receiving unit 190 has a function as a receiving unit receiving the input of the medical support work and the relief work designated by the user A2. The transmitting and receiving unit 190 can be made up of a module also provided with a wireless communication function such as a WiFi™ module and a Bluetooth™ module. The communication method of the transmitting and receiving unit 190 is not limited to the wireless communication described above. For example, contactless short-range wireless communication and wired communication may be adopted instead.

The four lift generating units 121a, 121b, 121c, and 121d placed at four corners of the upper housing 120 are disposed on the upper housing 120. The unmanned aerial vehicle 100 performs a movement in a vertical direction, a movement in a horizontal direction, hovering for staying for a certain period of time in the air, and the like by generating the lift by driving each of the lift generating units 121a, 121b, 121c, and 121d.

The lift generating units 121a to 121d may have no rotary blade and can generate the lift that is required for the unmanned aerial vehicle 100 to fly in the air by forming the air flow by means of air flow amplification based on the so-called Coanda effect.

The principle of the lift generation by the lift generating unit 121a will be briefly described with reference to FIGS. 5A and 5B. Note that, the lift generating units 121b to 121d are similar in shape and configuration to the lift generating unit 121a, and thus description of the lift generating units 121b to 121d will be omitted herein.

Figure 5A:
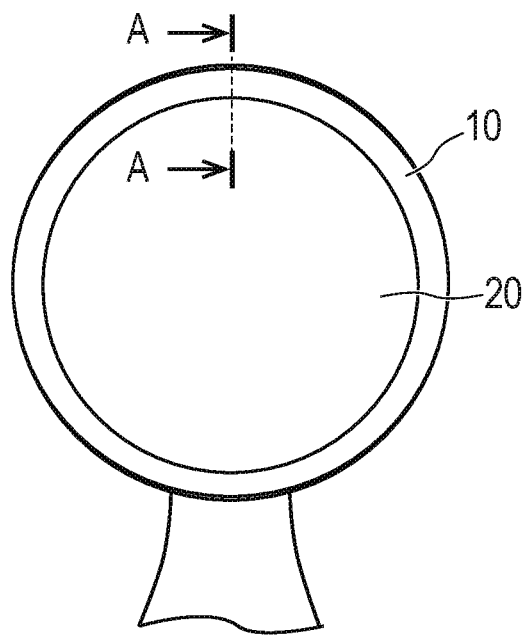
FIG. 5A is a front view of a lift generating unit according to embodiments of the present disclosure.

As illustrated in FIG. 5A, the lift generating unit 121a has an annular nozzle 10 that defines a middle opening portion 20. The drive unit 150 aforementioned generates an air flow through an internal flow path 11 of the nozzle 10 by, for example, rotationally driving the impeller by using the motor. The air flow becomes a drive force for the lift generating unit 121a to generate the lift.

Figure 5B:
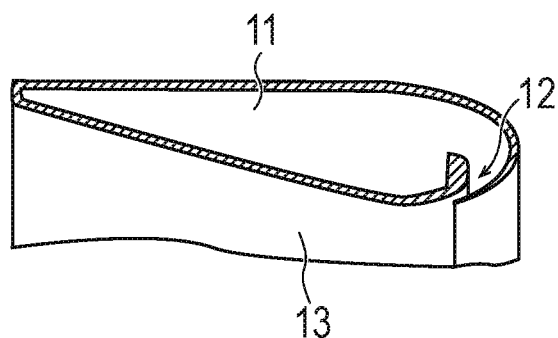
FIG. 5B is a sectional view of the lift generating unit taken along line A-A of FIG. 5A according to embodiments of the present disclosure.

As illustrated in FIG. 5B, the nozzle 10 has the internal flow path 11 through which the air flows, an outlet port 12 allowing the air flowing from the internal flow path 11 to flow to the outside, and a guiding surface 13 disposed adjacent to the outlet port 12 and guiding the air flow. The guiding surface 13 is configured to amplify the flow of the air coming out from the outlet port 12 and flowing on the guiding surface 13 by the Coanda effect. The amplified air flow forms an air flow through the middle opening portion 20. The lift generating unit 121a generates the lift from this air flow.

In the standby state of the normal mode, the unmanned aerial vehicle 100 stands by on the installation stand T, which is installed in the hospital, the public facility, or the like, as illustrated in FIG. 1A. Note that, a charging function can be added to the installation stand T. By the charging function being added to the installation stand T, wired or wireless charging of the unmanned aerial vehicle 100 can be performed while the unmanned aerial vehicle 100 stands by.

The configuration of each portion of the unmanned aerial vehicle 100 (the layout, dimension, color, exterior design, and the like of each member constituting unmanned aerial vehicle 100), materials constituting the respective portions of the unmanned aerial vehicle 100, and the like are not particularly limited insofar as the medical support work and the relief work by the unmanned aerial vehicle 100 can be executed. For example, an arm capable of gripping the article may be disposed on the load receiving unit 116 of the unmanned aerial vehicle 100 and the display unit 112, the speaker 113, and the like may be placed on a side surface or the like as well as a front face of the main body portion 110.

Hereinafter, an internal structure of the unmanned aerial vehicle 100 will be described with reference to FIG. 4A. FIG. 4A is a block diagram schematically illustrating the internal structure of the unmanned aerial vehicle 100.

As illustrated in FIG. 4A, the unmanned aerial vehicle 100 has the control unit 130 comprehensively controlling operations of the unmanned aerial vehicle 100. The control unit 130 has the CPU performing calculation processing, a read only memory (ROM) storing the operation program, a random access memory (RAM) (equivalent to a storage unit) for storing various types of data, and an electrically erasable programmable read-only memory (EEPROM) storing image data and sound data.

The control unit 130 functions as an output control unit 131 controlling content output by the display unit 112 and the speaker 113, a drive control unit 132 controlling the drive unit 150, and an imaging control unit 133 controlling the imaging unit 117 by executing the operation program stored in the ROM.

The output control unit 131 performs control for outputting a predetermined image such as the still image and the moving image on the display unit 112 and control for outputting a sound such as voice and music by using the speaker 113 based on the operation program. The image output on the display unit 112 and the sound output by the speaker 113 are appropriately output depending on content of the medical support work and the relief work designated by the user A2.

The drive control unit 132 controls the movement of the unmanned aerial vehicle 100 based on information on the location of the unmanned aerial vehicle 100. Objects controlled by the drive control unit 132 include the altitude and velocity of the unmanned aerial vehicle 100 during the unmanned aerial vehicle's movement and movement paths for reaching the destination from a place where the unmanned aerial vehicle 100 stands by (a movement path toward the medical site where the medical support work is executed and a movement path toward the disaster site where the relief work is executed). Note that, the movement path toward a disaster site P2 where the relief work is executed is obtained by calculation of the shortest path from a standby place P1 to the disaster site P2 based on map information stored in advance in the RAM before the execution of the relief work by the unmanned aerial vehicle 100 (refer to FIG. 10). The drive control unit 132 teaches the movement path of the unmanned aerial vehicle 100 based on the calculated content.

The imaging control unit 133 controls each of constituting members provided in the imaging unit 117 such as the imaging unit's lens, shutter, aperture, focus, and/or zoom. For example, the imaging control unit 133 performs control for a change in lens direction (direction of the lens) and viewing angle adjustment based on a change in the posture of the unmanned aerial vehicle 100 without the lens direction change.

Examples of the medical support work that the unmanned aerial vehicle 100 executes based on the medical support operation program can include at least one of "information transmission between health care workers", "information transmission between health care worker and recipient of medical service provided by the health care worker", "article transport", and/or "patient motion assistance".

Examples of the "information transmission between health care workers" include instruction transmission from a doctor to a nurse, reporting work from a nurse to a doctor, reporting work between doctors, dispensing discrimination work performed between pharmacists, and/or instruction transmission from a doctor to a pharmacist.

Examples of the "information transmission between health care worker and recipient of medical service provided by the health care worker" include patient examination by a doctor, examination result reporting from a doctor to a patient, and/or medicine management guidance work by a pharmacist.

Examples of the "article transport" include transport of articles for medical use (such as medical equipment, medicine, clinical records, and storage mediums like CDs and DVDs storing various types of data acquired by inspection) between hospital rooms, medicine transport from a pharmacist to a patient, and/or medicine transport from a pharmacy to a home care patient.

Examples of the "patient motion assistance" include patient motion assistance for walking, patient motion assistance for standing up from a bed, patient motion assistance for sitting on or lying in a bed, patient motion assistance for standing up from a wheelchair, and/or patient motion assistance for sitting in a wheelchair.

Examples of the relief work that the unmanned aerial vehicle 100 executes based on the operation program according to the present embodiment can include at least one of "victim state confirmation" and/or "medical treatment with respect to victim".

Examples of the "victim state confirmation" described above include the measurement of the bioinformation such as his or her blood pressure and pulse, confirmation as to the presence or absence of respiration, and/or diagnosis based on an interview and viewing.

Examples of the "medical treatment with respect to victim" described above include cardioversion, cardiac massage, and/or artificial respiration.

Note that, the medical support work and the relief work executed by the unmanned aerial vehicle 100 may have any content insofar as these are equivalent to treatment and work required for supporting the health care worker B2 and the victim B3 at the medical site and the disaster site and the examples described above do not limit the specific content of the work. Examples of the user A2 can include rescue workers, doctors, nurses, pharmacists, physical therapists, occupational therapists, caregivers, medical clerks, and central government, prefectural, and/or municipal officials. The user A2 is not limited to the examples though, and the examples may also include volunteer staff and those executing speed processing distribution (SPD) work to supply medical facilities with supplies such as medical consumables.

Figure 4B:
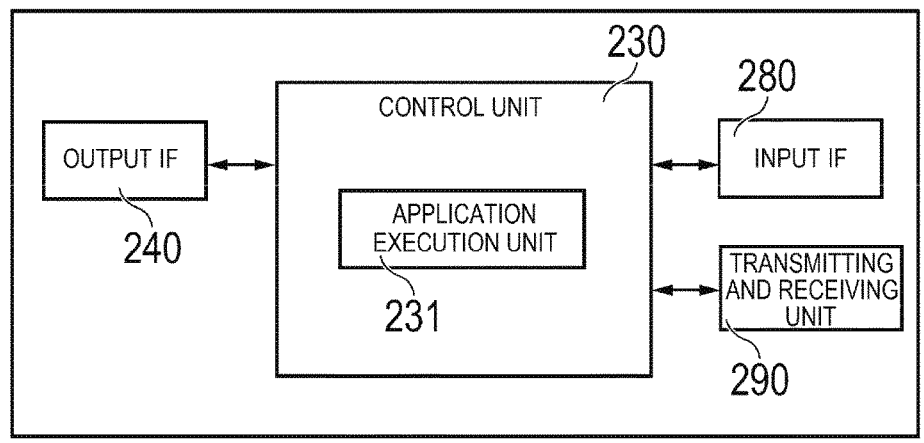

Hereinafter, an internal structure of the information terminal device 200 will be described with reference to FIG. 4B. FIG. 4B is a block diagram schematically illustrating the internal structure of the information terminal device 200.

As illustrated in FIG. 4B, the information terminal device 200 has a control unit 230 comprehensively controlling operations of the information terminal device 200, an output interface 240, an input interface 280, and/or a transmitting and receiving unit 290. Note that, some configurations such as an imaging unit are not illustrated in FIG. 4B.

The control unit 230 has the CPU performing calculation processing, a ROM storing a predetermined application, a RAM for storing various types of data, and an EEPROM storing image data and sound data.

The output interface 240 can be made up of, for example, a display unit capable of displaying an image or the like and a speaker capable of outputting sounds including voice and music. The display unit and the speaker can have a similar configuration to, for example, those disposed in the unmanned aerial vehicle 100.

The input interface 280 can be made up of a capacitive touch panel also provided with a function as a display unit capable of displaying an image. The input interface 280 can also be made up of, for example, an operation button allowing a user operation input and a microphone allowing a voice input.

The transmitting and receiving unit 290 performs data transmission and reception via a wireless communication network and transmits the transmission command to the unmanned aerial vehicle 100. The transmitting and receiving unit 290 can have a similar configuration to, for example, the wireless module disposed in the unmanned aerial vehicle 100.

The control unit 230 has a function as an application execution unit 231 executing an application. The application can be made up of, for example, a general operating system (OS) and browser software.

In a case where the medical support work or the relief work is allowed to be executed by the unmanned aerial vehicle 100, the user A2 starts the application on the information terminal device 200 by operating the information terminal device 200. By operating the information terminal device 200, the user A2 selects the medical support work or the relief work to be executed by the unmanned aerial vehicle 100. The information terminal device 200 transmits a result of the selection by the user A2 to the unmanned aerial vehicle 100, through the wireless communication network, and as the transmission command. The unmanned aerial vehicle 100 receives the transmission command via the transmitting and receiving unit (receiving unit) 190 and receives the work content. After receiving the work content, the unmanned aerial vehicle 100 executes the medical support work or the relief work in accordance with the selected work content.

Figure 6:
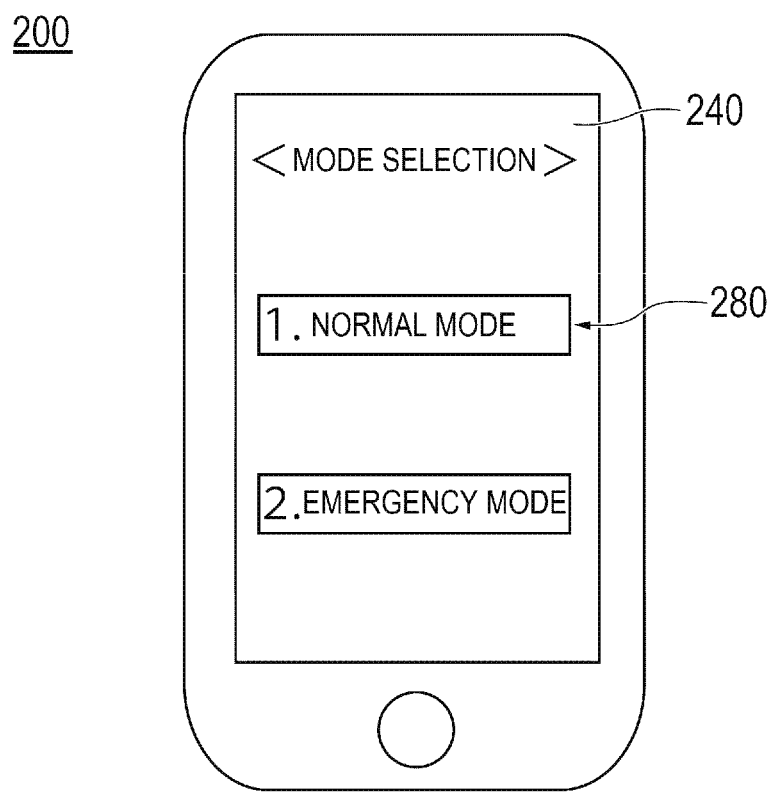
FIG. 6 is a diagram illustrating an example of a selection screen displayed on the information terminal device according to embodiments of the present disclosure.

An example of a selection screen displayed on the output interface (IF) (display unit) 240 of the information terminal device 200 is illustrated in FIGS. 6 to 8.

"Mode selection screen" illustrated in FIG. 6 is displayed once the application is started on the information terminal device 200. The user A2 selects the "normal mode" or the "emergency mode" on this selection screen. The selection can be performed by the input IF (touch panel function on the display unit) 280 being used.

Figure 7A:
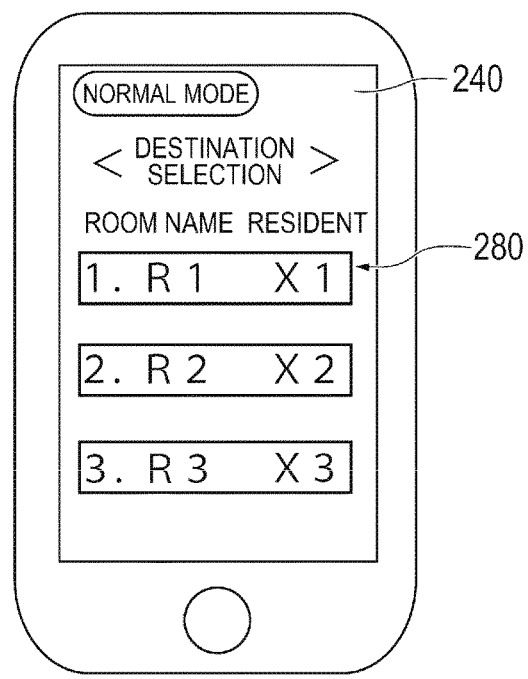
FIGS. 7A and 7B are diagrams illustrating an example of the selection screen displayed on the information terminal device according to embodiments of the present disclosure.

"Destination selection screen" illustrated in FIG. 7A is displayed in a case where the "normal mode" is selected by the user A2. The destination selection screen displays, for example, the names of rooms in the hospital and the names of residents in the rooms. The user A2, who is a health care worker, confirms the destination of the unmanned aerial vehicle 100 and an object person on this selection screen and selects desired content.

Figure 7B:
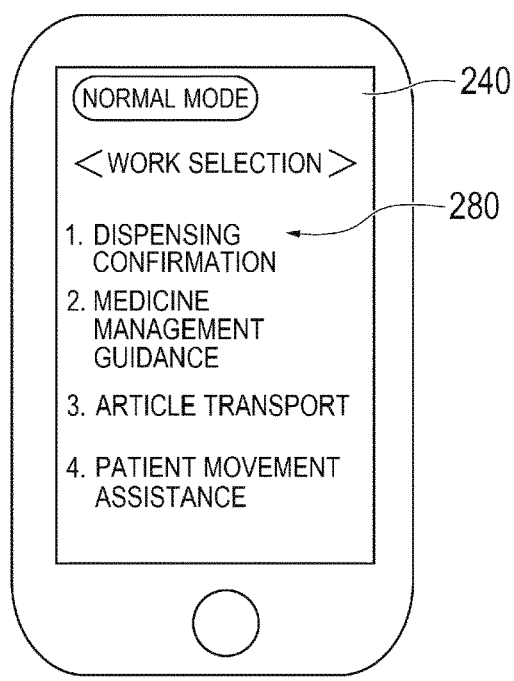

"Work selection screen" illustrated in FIG. 7B is displayed once the destination is selected on the "destination selection screen". The user A2 selects the content of the medical support work to be executed by the unmanned aerial vehicle 100 on this selection screen.

Once the user A2 selects the medical support work content, the medical support application displays a confirmation screen for a confirmation of whether to execute extra medical support work. Once the user A2 performs an input to the effect of extra medical support work execution, the medical support application displays the "destination selection screen" illustrated in FIG. 7A again and receives destination selection. In a case where no extra medical support work is executed, the medical support application receives the effect and then completes input receipt.

In a case where both the destination and the work content have been selected by the user A2, the medical support work of the unmanned aerial vehicle 100 is continuously executed in accordance with the order of the selection.

Update of information related to the destination, update of information related to the residents (supported persons), update of the medical support application, and the like can be regularly or irregularly performed via, for example, the management server 300. In a case where the object person's place of stay has changed and in a case where the medical support work that can be provided for the object person has changed, for example, update can be performed such that display content of each selection screen of the medical support application changes in accordance with content of the changes.

Hereinafter, the content of the medical support work that can be executed by the unmanned aerial vehicle 100 according to embodiments of the present disclosure will be described. The unmanned aerial vehicle 100 is configured to be capable of executing the four types of work content that are illustrated in FIG. 7B.

"Dispensing confirmation" is work performed for the purpose of preventing an error occurring throughout dispensing work performed by a pharmacist. Inspection is an example of work performed by pharmacists. The inspection is performed by a pharmacist other than the pharmacist performing the medicine dispensing (preparation) and is work for determining whether dispensing content or the like is free from errors. In a case where the dispensing pharmacist has little experience, checking by the other pharmacist is performed so that whether the dispensing content is free from errors is to be found out. The "dispensing confirmation" includes these types of confirmation work supposed to be performed by pharmacists. In a case where the dispensed medicine is confirmed, involvement of the pharmacist other than the dispensing pharmacist is required, and thus a plurality of pharmacists has to be ensured as personnel. The use of the unmanned aerial vehicle 100 allows the dispensing confirmation to be smoothly and quickly performed even in a case where no extra pharmacist is available around the dispensing pharmacist and in a case where the other pharmacist has no time to spare because of circumstances such as a busy season.

"Medicine management guidance" is support work for improving patients' drug therapy awareness via inpatient medication history management and inpatient medication guidance. This work is usually performed face to face between a pharmacist and an inpatient. Accordingly, the pharmacist himself or herself is required to visit a ward or the like where the inpatient stays and spend his or her time on explanation. In a case where the pharmacist has no time to spare and a sufficient length of time is rarely available, no time can be spared for the visit to the patient for the explanation by the pharmacist himself or herself as the case may be. With the unmanned aerial vehicle 100, waste of time attributable to place-related constraints can be suppressed, and thus time spent on the medicine management guidance by pharmacists can be ensured.

"Article transport" is work for assisting in the transport of an article such as medicine, a medical appliance, and a clinical record (refer to FIG. 8). The work burden of a nurse and the like can be reduced by the article being transported between the different rooms in the hospital based on the use of the unmanned aerial vehicle 100. Note that, specific examples of the transport work include work for delivering medicine brought by an inpatient to the inpatient, work for delivering medicine to be taken soon to an inpatient, and/or work for collecting unnecessary medicine from a patient.

"Patient motion assistance" is, for example, work for providing ambulatory assistance for a patient receiving an intravenous drip. When the unmanned aerial vehicle 100 is moved in step with the ambulation of the patient with an intravenous drip bag held by the unmanned aerial vehicle 100, the patient can be guided to a toilet or the like without an intravenous drip stand or the like being carried around. Since the unmanned aerial vehicle 100 is afloat and moves in the air, the unmanned aerial vehicle 100 is hindered by nothing even when the patient goes up in a stairway and is capable of helping the patient so that his or her ambulation is smooth. In a case where a movement of a patient relying on a wheelchair is assisted in based on the use of the unmanned aerial vehicle 100, the patient does not have to carry around an intravenous drip stand, and thus a smooth wheelchair movement can be realized.

Figure 8A:
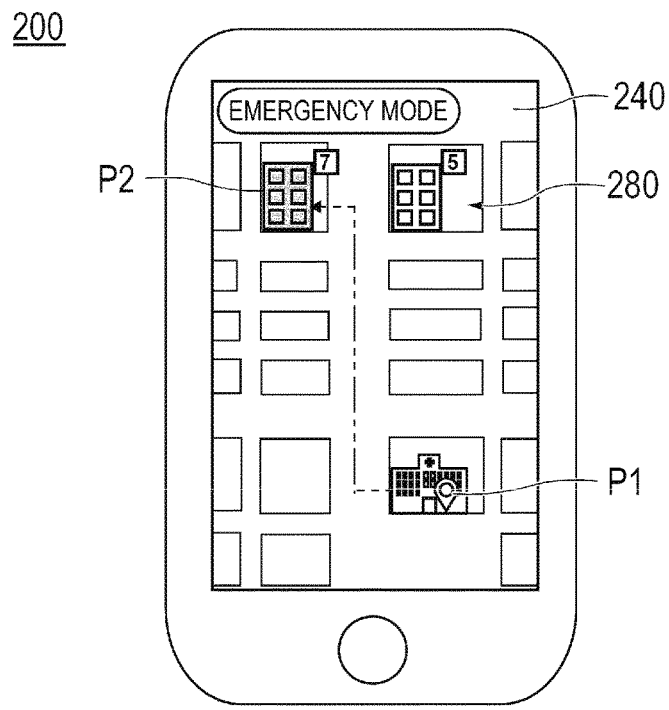
FIGS. 8A and 8B are diagrams illustrating an example of the selection screen displayed on the information terminal device according to embodiments of the present disclosure.

The "destination selection screen" that is illustrated in FIG. 8A is displayed in a case where the "emergency mode" is selected by the user A2 (refer to FIG. 6). In the destination selection screen, the user A2 confirms the disaster site P2 of the unmanned aerial vehicle 100 on this selection screen. In a case where disasters have occurred at a plurality of places, the user A2 can select the disaster site P2, which is one of the plurality of places where the disasters have occurred, as the destination.

Display in the "destination selection screen" may, for example, be based on different colors or numerical values indicating seismic intensities, magnitudes, and the like depending on the degrees of disasters or the degree of support shortage so that a difference in the degrees of emergency can be seen at a glance. In this manner, the user A2 can select the destination in accordance with the degrees of emergency.

Figure 8B:
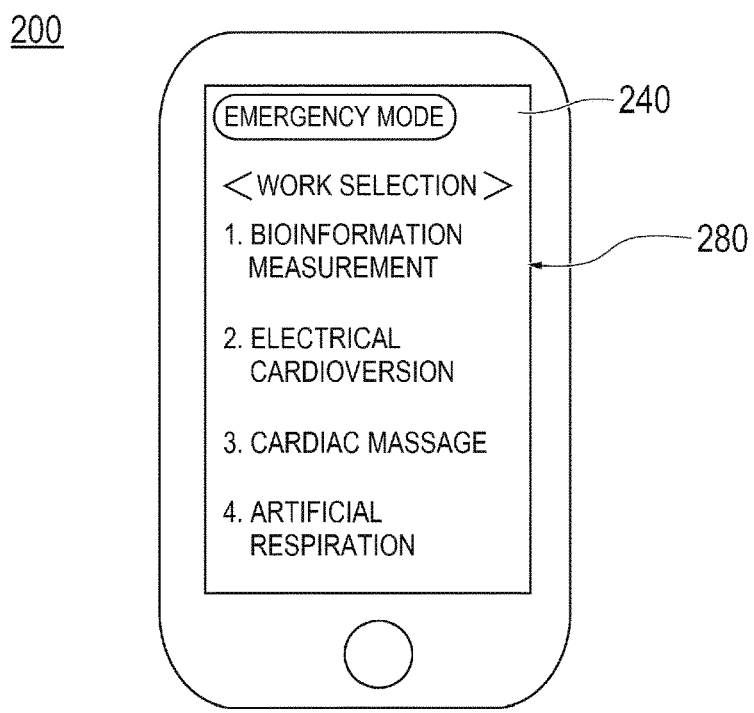

"Work selection screen" illustrated in FIG. 8B is displayed once the destination is selected on the "destination selection screen". The user A2 selects the content of the relief work to be executed by the unmanned aerial vehicle 100 on this selection screen.

In a case where both the destination and the work content have been selected by the user A2, the relief work of the unmanned aerial vehicle 100 can be continuously executed in accordance with the order of the selection.

Update of the map information, update of weather information, update of the application, and the like can be regularly or irregularly performed via, for example, the management server 300. In a case where a building or a road on the map has changed and in a case where the execution of the relief work is impossible due to bad weather, for example, update can be performed such that display content of each selection screen of the application changes in accordance with content of the changes.

Note that, the selection screen and application execution content and the like illustrated in FIGS. 6 to 8 are merely one example and can be appropriately changed.

Hereinafter, the content of the relief work that can be executed by the unmanned aerial vehicle 100 according to the present embodiment will be described. The unmanned aerial vehicle 100 is configured to be capable of executing the four types of work content that are illustrated in FIG. 8B.

"Bioinformation measurement" is work for measuring bioinformation, for example, electrocardiograms, heart rates, blood pressures, and/or body temperatures.

"Cardioversion" is work for recovering the function of a person's heart by applying an electric shock (defibrillation) to the person in a state of cardiopulmonary arrest.

"Cardiac massage" is work for performing an automatic cardiac massage treatment by using an automatic cardiac massager.

"Artificial respiration" is work for performing an automatic artificial respiration treatment by using an artificial respirator.

During the execution of the "bioinformation measurement", "cardioversion", "cardiac massage", and "artificial respiration", the unmanned aerial vehicle 100 performs treatment content reporting and description with respect to the victim B3 and a rescuer at the site by displaying a predetermined display image in the display unit 112 or outputting a sound from the speaker 113. During the reporting and description, the unmanned aerial vehicle 100 may output an image preserved in advance (still image and/or moving image) or output the image and voice of the user A2 in real time through the transmitting and receiving unit 290 of the information terminal device 200.

Note that, the "bioinformation measurement", "cardioversion", "cardiac massage", and "artificial respiration" can be simultaneously executed. Accordingly, input receipt may be simultaneously performed with, for example, the other work on the application aforementioned.

In a case where it is difficult for a person to approach the disaster site due to an earthquake, a landslide, or the like, for example, searching for the victim B3 in need of relief can be performed by the detection unit 160 (refer to FIG. 4A) that the unmanned aerial vehicle 100 is equipped with. The unmanned aerial vehicle 100 is capable of sending an image of the disaster site captured from the sky by the imaging unit 117 to the information terminal device 200 via the transmitting and receiving unit 290. The user A2 can search for the victim B3 by checking the image. Note that, the control unit 230 may perform work such as image analysis and then transmit a result of the analysis to the user A2 via the output interface 240.

The control unit 130 controls the movement of the unmanned aerial vehicle 100 based on the input data such that contact with obstacles and the like is avoided. In addition, the control unit 130 is capable of controlling the movement of the unmanned aerial vehicle 100 such that the contact with the obstacles is avoided by, for example, performing the movement while detecting the presence or absence of the obstacles by using the detection unit 160 that the unmanned aerial vehicle 100 is equipped with.

Hereinafter, an example of the execution of the work by the unmanned aerial vehicle 100 will be described with reference to FIGS. 9 and 10.

Figure 9:
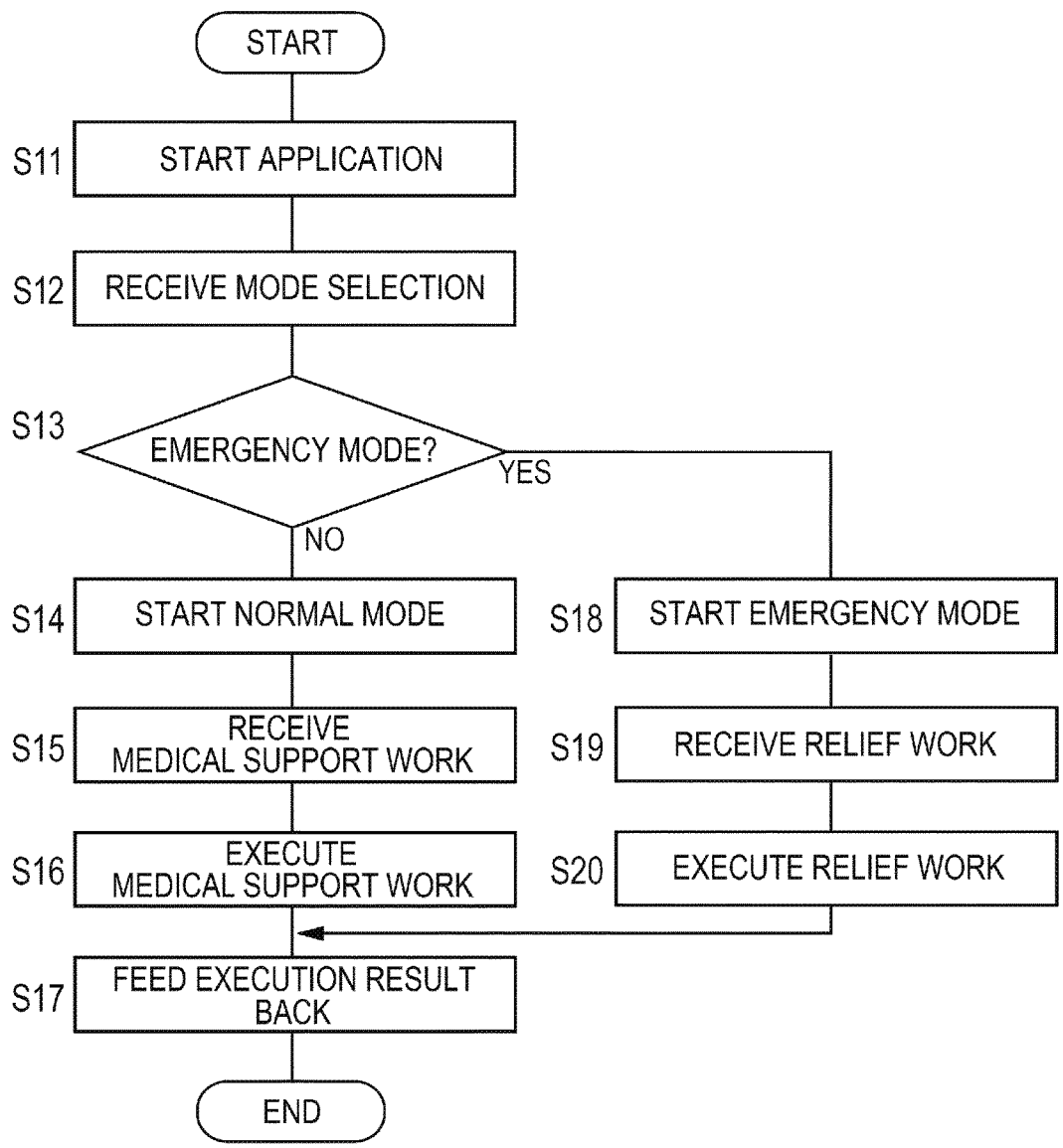
FIG. 9 is a flowchart illustrating a procedure example at a time when medical support work or relief work is performed according to embodiments of the present disclosure.

FIG. 9 shows a procedure example at a time when the work is performed.

In allowing the medical support work or the relief work to be executed by the unmanned aerial vehicle 100, the user A2 starts the application on the information terminal device 200 (S11). Then, the user A2 selects the normal mode or the emergency mode on the application as aforementioned. The selection result is transmitted as the transmission command from the information terminal device 200 to the unmanned aerial vehicle 100. The unmanned aerial vehicle 100 receives the input of the mode selection based on the transmission command (S12).

In a case where the unmanned aerial vehicle 100 has received the selection of the normal mode from the user A2 (S13: NO), the screen of the normal mode is started on the information terminal device 200 (S14). Then, the user A2 selects the medical support work. The selection result is transmitted as the transmission command from the information terminal device 200 to the unmanned aerial vehicle 100. The unmanned aerial vehicle 100 receives the input of the medical support work content based on the transmission command (S15). Once the receipt of the input of the medical support work content is completed, the unmanned aerial vehicle 100 executes the medical support work (S16). After the execution of the medical support work, the unmanned aerial vehicle 100 performs feedback of execution result with respect to the user A2 (S17).

In a case where the unmanned aerial vehicle 100 has received the selection of the emergency mode from the user A2 (S13: YES), the screen of the emergency mode is started on the information terminal device 200 (S18). Then, the user A2 selects the relief work. The selection result is transmitted as the transmission command from the information terminal device 200 to the unmanned aerial vehicle 100. The unmanned aerial vehicle 100 receives the input of the relief work content based on the transmission command (S19). Once the receipt of the input of the relief work content is completed, the unmanned aerial vehicle 100 executes the relief work (S20). After the execution of the relief work, the unmanned aerial vehicle 100 performs execution result feedback with respect to the user A2 (S17).

Figure 10:
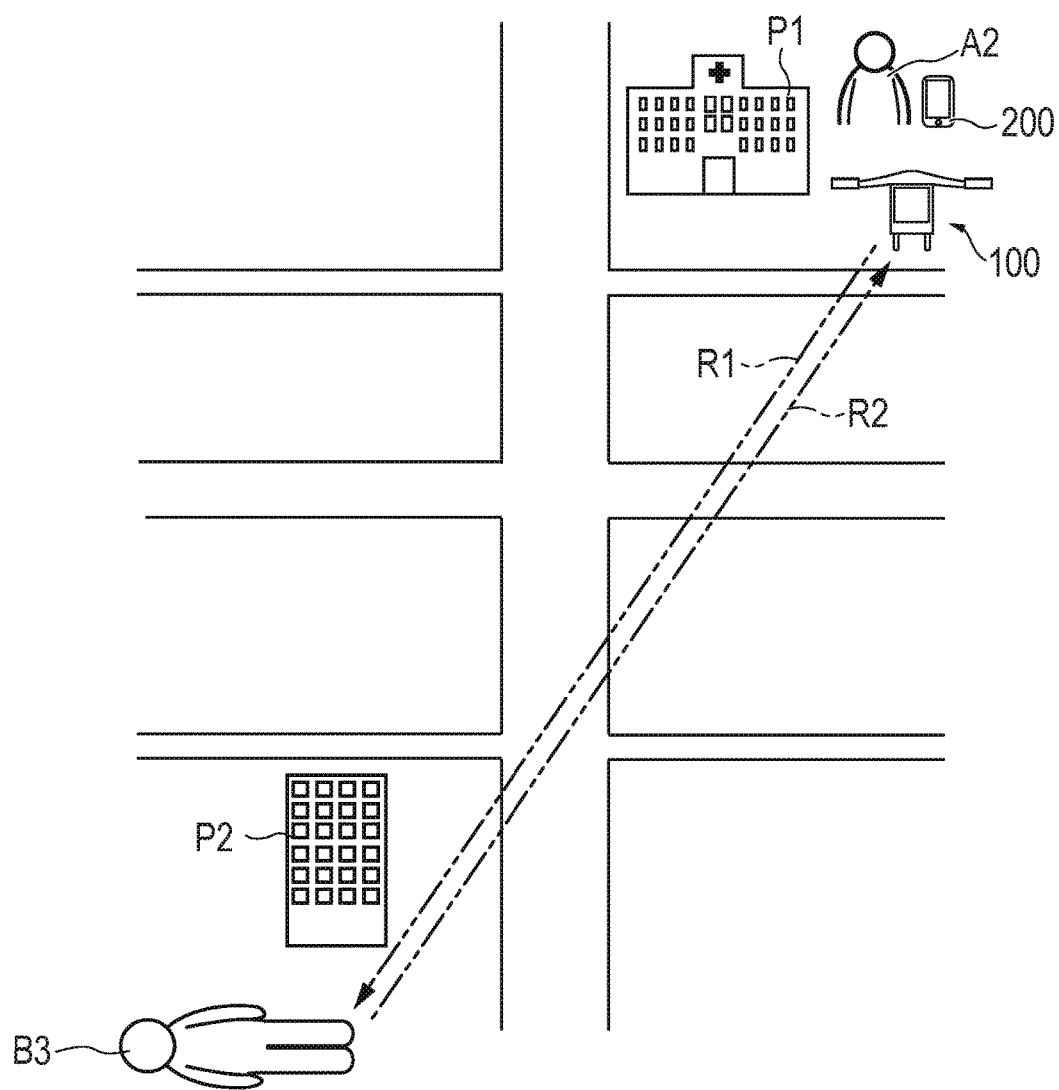
FIG. 10 is a diagram for showing a movement path of the unmanned aerial vehicle according to embodiments of the present disclosure.

FIG. 10 shows an example of the use of the unmanned aerial vehicle 100 at the disaster site.

In the example that is illustrated in FIG. 10, the user A2 allows the unmanned aerial vehicle 100 to execute the "bioinformation measurement" and the "cardioversion". The unmanned aerial vehicle 100 performs the "bioinformation measurement" on the victim B3, and then determines the necessity of the "cardioversion" from the result and performs the "cardioversion" with respect to the victim B3. Note that, in this example, the user A2 is a health care worker normally staying in the hospital (such as a paramedic, a doctor, a nurse, and a caregiver). The victim B3 is in a state of unconsciousness in the wake of an injury in a natural disaster such as an earthquake.

Before the relief work is performed, the unmanned aerial vehicle 100 stands by at the standby place P1 in the hospital where the user A2 normally stays. In the standby state, the unmanned aerial vehicle 100 is installed on the installation stand T (refer to FIG. 1A) at the standby place P1 and can be used as the medical equipment 111a to 111d. In a case where the user A2 is not nearby the standby place P1 when an emergency has occurred, the user A2 can remotely control the unmanned aerial vehicle 100.

Upon receiving the work content selected by the user A2, the unmanned aerial vehicle 100 leaves the standby place P1, moves along a movement path R1, and heads for the disaster site P2. Note that, each of the movement paths R1 and R2 that are illustrated in the drawing is the shortest path between the standby place P1 and the disaster site P2 obtained as a result of the CPU-based calculation processing based on the location information on the disaster site P2 received by the transmitting and receiving unit 190.

Upon reaching the disaster site P2, the unmanned aerial vehicle 100 checks the situation of the disaster site P2 via the imaging unit 117. Before the work is initiated, the unmanned aerial vehicle 100 checks the situation of the disaster site P2 such as the presence or absence of the danger of the occurrence of a secondary disaster around the victim B3 that is attributable to the collapse of a building or a fire. This confirmation can be performed by, for example, the user A2 performing visual confirmation with the image captured via the imaging unit 117 or direct confirmation being performed for a person around the victim B3 via the speaker 113 and the microphone 114.

After the unmanned aerial vehicle 100 confirms the situation of the disaster site P2, the unmanned aerial vehicle 100 initiates the work. The unmanned aerial vehicle 100 checks the state of the victim B3 first via the speaker 113, the microphone 114, the imaging unit 117, and the like. Once it is confirmed that the victim B3 is in a state of unconsciousness, the "bioinformation measurement" is executed and the blood pressure, pulse, and the like of the victim B3 are measured.

Once it is confirmed from results of the measurement that the victim B3 is in a state of cardiopulmonary arrest and it is determined that the "cardioversion" is required, the user A2 allows the unmanned aerial vehicle 100 to execute the cardioversion.

The unmanned aerial vehicle 100 brings the electrode pad of the automated external defibrillator 111b into contact with the chest of the victim B3 first. The electrode pad is fixed to the chest of the victim B3 via an adhesive-applied adhesion surface. Note that, the electrode pad fixing operation may be automatically performed by a medical equipment drive unit of the unmanned aerial vehicle 100 or may be performed by a rescuer nearby the victim B3. Subsequently, the automated external defibrillator 111b is operated and an electric shock is applied to the heart of the victim. B3 by the cardioversion. In this manner, the cardioversion, which is emergency treatment for heart function recovery, is performed.

Once the termination of the cardioversion is confirmed, the unmanned aerial vehicle 100 moves along the movement path R2 from the disaster site P2 and returns to the standby place P1.

After the returning to the standby place P1, the unmanned aerial vehicle 100 feeds the results of the execution of the "bioinformation measurement" and the "cardioversion" back to the user A2. The feedback can be performed by, for example, the display of an image indicating that the work has been successfully completed on the display unit 112 or the display of an image indicating that some of the work has yet to be executed on the display unit 112. Results of the feedback can be transmitted to the management server 300 and preserved therein.

Hereinafter, effects of the embodiments described herein will be described.

The unmanned aerial vehicle 100, according to embodiments of the present disclosure, has the transmitting and receiving unit (receiving unit) 190 receiving the input of the relief work from the user A2 and the control unit 130 controlling the execution of the relief work with respect to the victim (relief recipient) B3 based on the input content received by the transmitting and receiving unit 190.

In a case where a disaster has occurred, for example, the unmanned aerial vehicle 100 moves directly to the disaster site and executes the relief work following the processing content that is designated by the user A2 with respect to the victim B3. Since the unmanned aerial vehicle 100 is capable of moving in the air, the unmanned aerial vehicle 100 is capable of quickly moving in the shortest path to the disaster site regardless of the traffic situation around the disaster site. In this manner, appropriate relief work can be quickly executed with respect to the victim B3 in need of emergency relief from, for example, a state of cardiopulmonary arrest.

The unmanned aerial vehicle 100 is configured to be capable of selectively switching between the normal mode, which is the standby state where no work is executed or the operating state where the medical support work (task support work) is performed, and the emergency mode, which is the operating state where the relief work is performed. Accordingly, in the standby state of the normal mode, the user A2 can use the unmanned aerial vehicle 100 as the medical equipment 111a to 111d. In addition, in the operating state of the normal mode, the unmanned aerial vehicle 100 is capable of executing the medical support work following the processing content designated by the user A2 at the medical site. By executing the medical support work, the unmanned aerial vehicle 100 assists in the work supposed to be performed by the user A2 or replaces the user A2. Accordingly, a decline in medical service quality attributable to labor shortage and so on can be suppressed and personnel expenses at the medical site can be reduced. In addition, in the emergency mode, the unmanned aerial vehicle 100 performs the relief work with respect to the victim B3 at the disaster site. In this manner, medical treatment such as the cardioversion can be quickly performed for the victim B3 in need of emergency treatment from cardiopulmonary arrest and so on. The scope of application of the unmanned aerial vehicle 100 can be widened in hospitals, public facilities, and the like, even in a case where the relief work by the unmanned aerial vehicle 100 is not required, based on the switching between the normal mode and the emergency mode described above.

The relief work that is executed by the unmanned aerial vehicle 100 includes at least one of the "victim state confirmation" and the "medical treatment with respect to victim". The user A2 can confirm the state of the victim B3 and perform the medical treatment with respect to the victim B3. In addition, the required medical treatment can be clarified based on the confirmation of the state of the victim B3 and appropriate medical treatment can be provided for the victim B3 when the "victim state confirmation" and the "medical treatment with respect to victim" are combined with each other. Accordingly, the relief work with respect to the victim B3 can be performed more effectively.

The "victim state confirmation", which constitutes the relief work executed by the unmanned aerial vehicle 100, includes the measurement of the bioinformation such as the blood pressure and pulse. Accordingly, the state of the victim B3 can be further accurately grasped. The "medical treatment with respect to victim" includes at least one of treatments based on the cardioversion and cardiopulmonary resuscitation. Accordingly, the treatment based on the cardioversion or cardiopulmonary resuscitation can be performed if necessary and urgent emergency treatment can be carried out.

A relief method according to the present embodiment includes a receiving step of receiving the processing content from the user A2 via the transmitting and receiving unit (receiving unit) 190 that the unmanned aerial vehicle 100 is provided with and a control step of controlling the execution of the relief work with respect to the victim. B3 in accordance with the processing content by the control unit 130 that the unmanned aerial vehicle 100 is provided with.

According to the method described above, the unmanned aerial vehicle 100 executes the relief work following the processing content that is designated by the user A2 at the disaster site. Since the unmanned aerial vehicle 100 is capable of moving in the air, the unmanned aerial vehicle 100 is capable of quickly moving in the shortest path to the disaster site regardless of the traffic situation around the disaster site. In this manner, appropriate relief work can be quickly executed with respect to the victim B3 in need of emergency relief from, for example, a state of cardiopulmonary arrest.

Additional or Alternative Embodiments

The relief work that the unmanned aerial vehicle executes based on the relief system is not limited to what has been described above. Regarding a relief system 1a according to another example, "oral environment improvement", which is an example of the "nursing", will be described as an example of the relief work that is executed by an unmanned aerial vehicle 100a.

Figure 11:
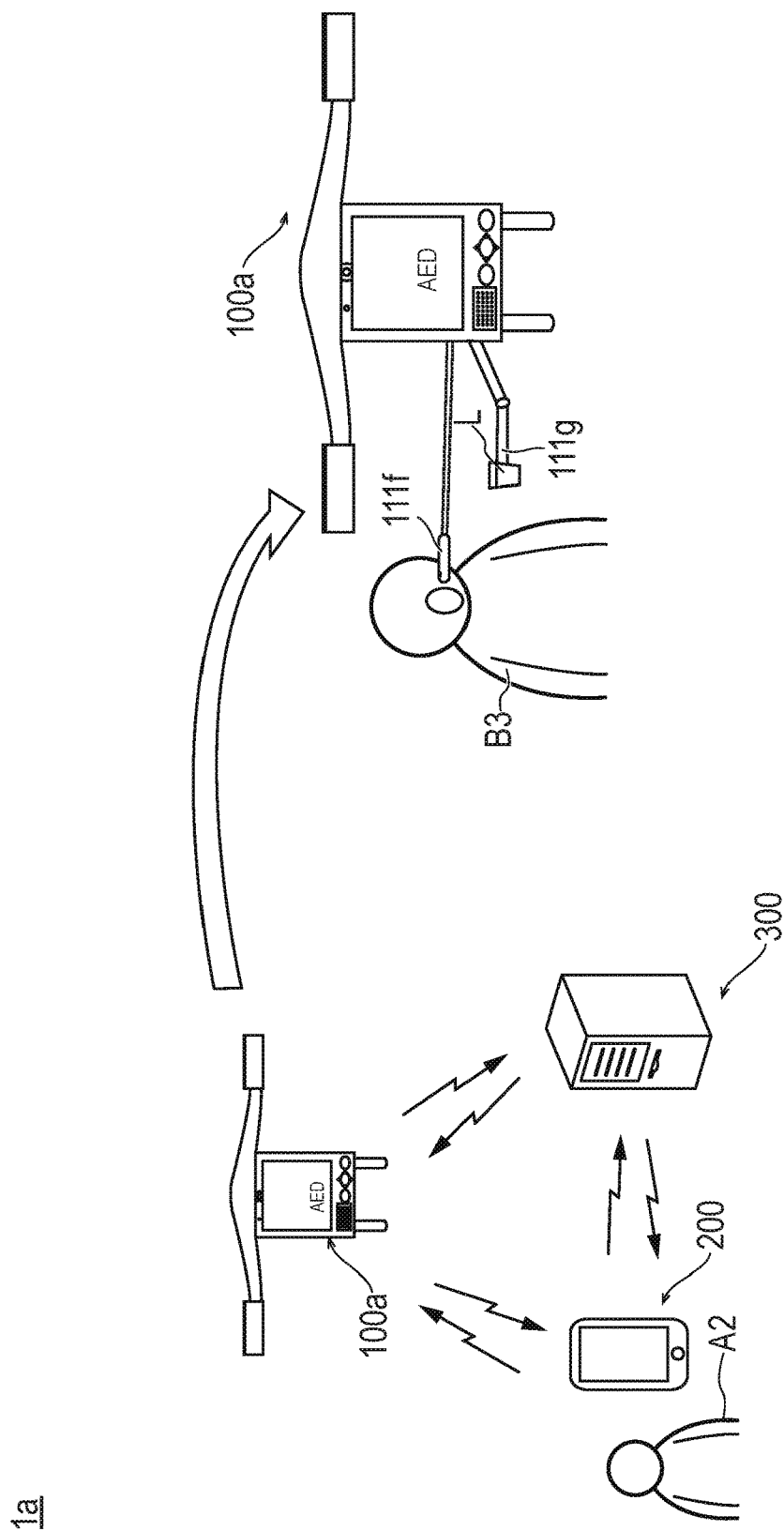
FIG. 11 is a diagram for showing medical support work of an unmanned aerial vehicle according to embodiments of the present disclosure.

As illustrated in FIG. 11, the unmanned aerial vehicle 100a according to the modification example has a halitosis measuring instrument 111f measuring halitosis and a supply section 111g supplying the victim. B3 with an oral care product L such as a mouthwash and a mouth disinfection sheet with which a container is filled.

Examples of the relief work that the unmanned aerial vehicle 100a executes based on an operation program according to the modification example can include at least one of the "victim state confirmation" and the "oral environment improvement".

Examples of the "victim state confirmation" described above include the measurement of the halitosis, which is bioinformation.

In addition, examples of the "oral environment improvement" described above include the providing of the oral care product L for mouth environment improvement.

The user A2 measures the halitosis of the victim B3 staying in, for example, an evacuation shelter by using the unmanned aerial vehicle 100a and performs the oral environment improvement by providing the oral care product L if necessary. In this manner, a deterioration of the oral environment of the victim B3 can be prevented during the living in the shelter over an extended period of time and diseases such as aspiration pneumonitis occurring when germs in the oral cavity enter the trachea can be prevented.

An unmanned aerial vehicle 400 according to another alternative or additional embodiment and a relief method based on the unmanned aerial vehicle 400 will be described with reference to FIGS. 12 to 14. In the aforementioned examples, the "treatment" and the "nursing" with respect to the victim B3 have been mainly described as examples of the relief work that the unmanned aerial vehicle executes based on the relief system. In another embodiment, "protection" of the victim B3 will be described as an example of the relief work. Note that, in the description of the second embodiment, description of those that have the same functions as the already described members and configurations will be appropriately omitted. Regarding points not particularly mentioned with regard to device configuration and control content, configuration similar to that of the aforementioned embodiment (s) can be carried out.

Figure 12A:
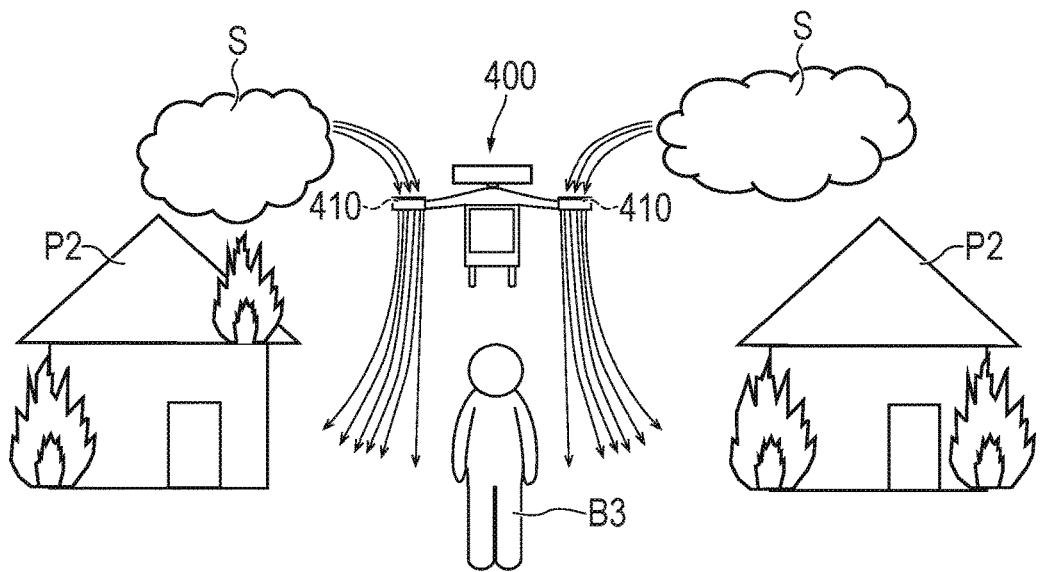
FIGS. 12A and 12B are conceptual diagrams for showing an example of relief work by an unmanned aerial vehicle according to embodiments of the present disclosure.
Figure 12B:
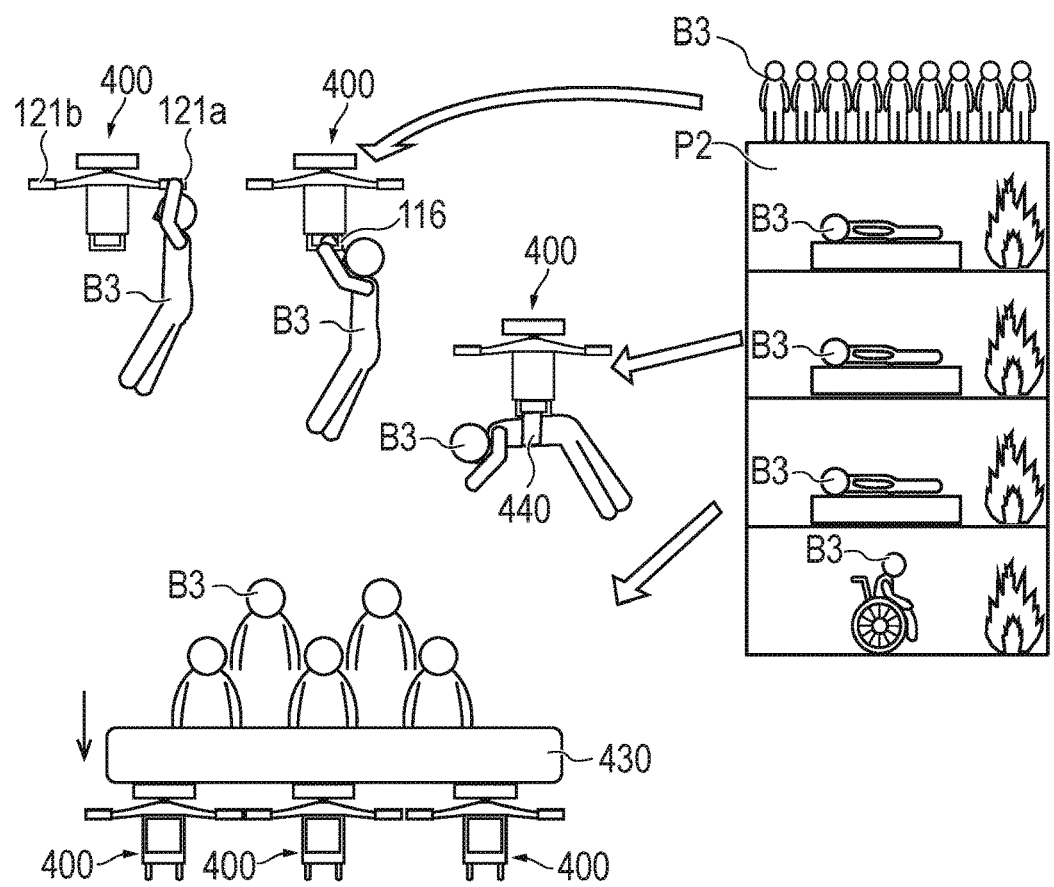

As in the aforementioned embodiment(s), the unmanned aerial vehicle 400 may stand by at a predetermined place as illustrated in FIG. 1A or executes the medical support work in the hospital that is illustrated in FIG. 1B. In the emergency mode, the unmanned aerial vehicle 400 executes the relief work at the disaster site as illustrated in FIGS. 12A and 12B. Note that a case where a fire has occurred will be described as an example of disasters.

Figure 13A:
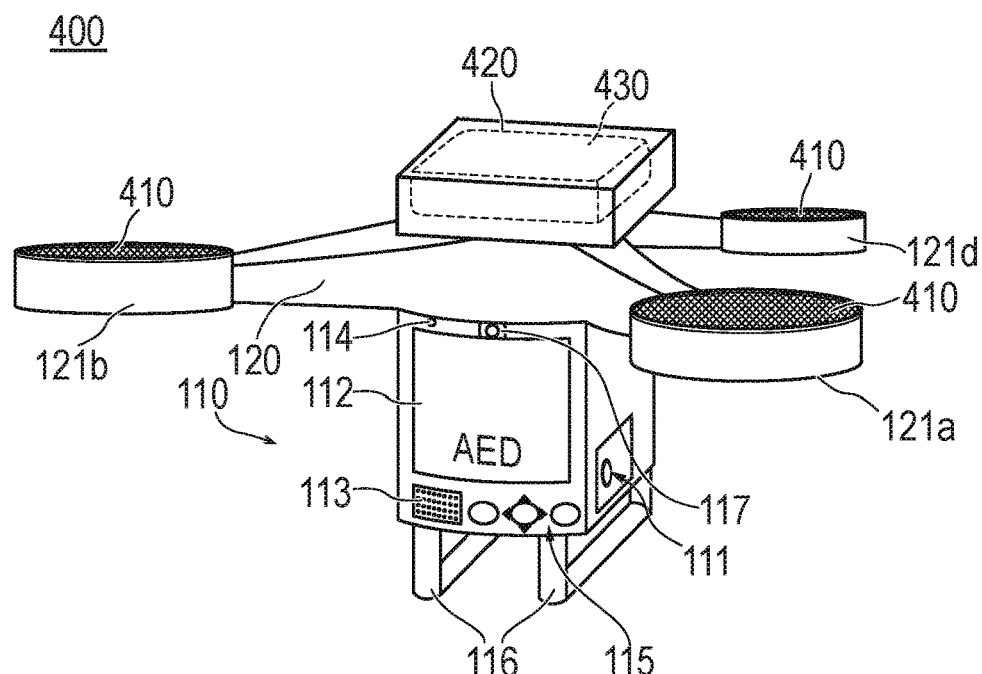
FIG. 13A is a perspective view of the unmanned aerial vehicle according to embodiments of the present disclosure.

As in the aforementioned embodiment(s), the unmanned aerial vehicle 400 is provided with the lift generating units 121a to 121d. As illustrated in FIG. 13A, smoke removal filters 410 are placed in the middle opening portions 20 of the lift generating units 121a to 121d. As a result, the lift generating units 121a to 121d are capable of guiding smoke resulting from the fire along with air to the smoke removal filters 410 by means of the air flow and removing the smoke via the smoke removal filters 410.

Figure 13B:
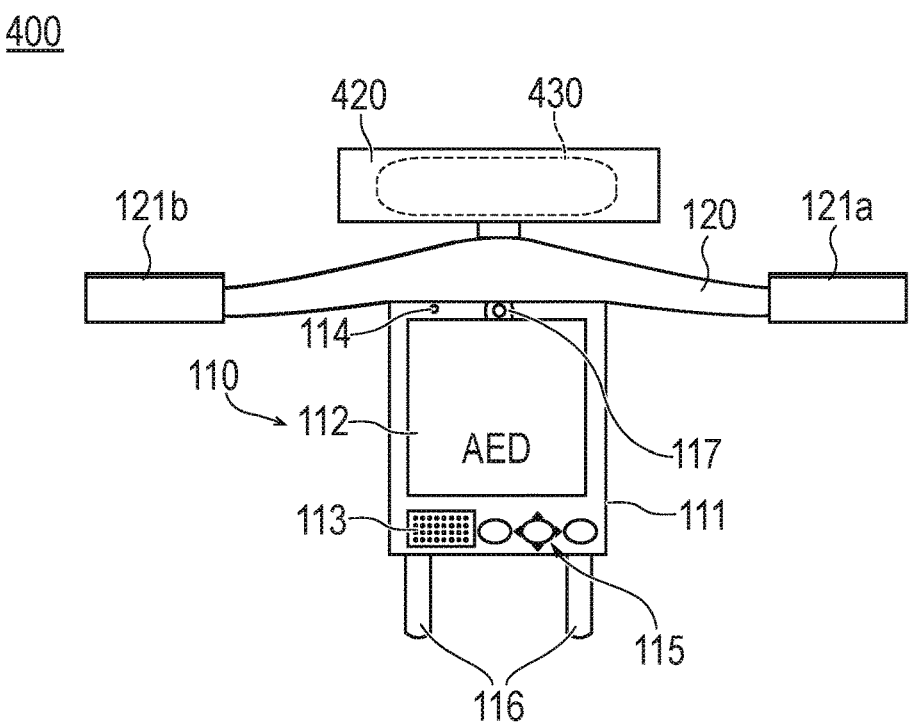
FIG. 13B is a front view of the unmanned aerial vehicle according to embodiments of the present disclosure.

In addition, the unmanned aerial vehicle 400 has a placement portion 420 fixed to an upper portion of the main body portion 110 and disposed to be capable of allowing a person and an article to be placed on itself, an airbag (shock absorbing unit) 430 accommodated in a folded state in the placement portion 420, and a fixing tool 440 capable of fixing the victim B3 to the load receiving unit 116 (refer to FIG. 12B) as illustrated in FIGS. 13A and 13B. The airbag 430 is configured to be deployed when gas is supplied into the airbag 430 and can protect the victim B3 from a landing impact.

The relief work that the unmanned aerial vehicle 400 according to the second embodiment executes based on the operation program can include at least one of "avoidance of dangers around victim" and "victim evacuation support".

Examples of the "avoidance of dangers around victim" described above include smoke removal and securing of air at the disaster site where the fire has occurred.

Examples of the "victim evacuation support" described above include support for escape of the victim B3 under adverse evacuation conditions from the disaster site.

In a case where the user A2 has selected the emergency mode on the selection screen displayed on the output IF (display unit) 240 of the information terminal device 200 (refer to FIG. 6), the "destination selection screen" is displayed as in the first embodiment (refer to FIG. 8A). The user A2 confirms the place where the disaster to be dealt with by the unmanned aerial vehicle 400 has occurred on this selection screen and selects the disaster site P2 as the destination.

Figure 14:
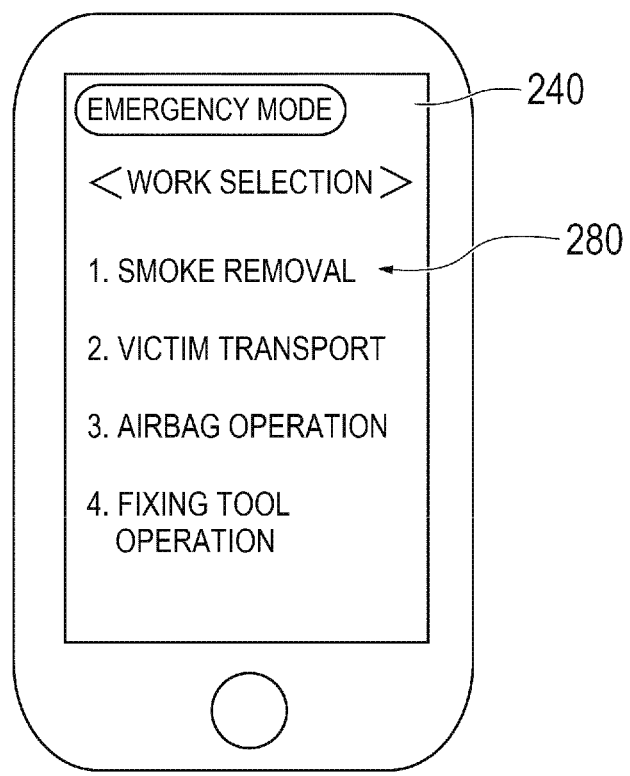
FIG. 14 is a diagram illustrating an example of a selection screen displayed on an information terminal device according to embodiments of the present disclosure.

"Work selection screen" illustrated in FIG. 14 is displayed once the destination is selected on the "destination selection screen". The user A2 selects the content of the relief work to be executed by the unmanned aerial vehicle 400 on this selection screen.

Hereinafter, the content of the relief work that can be executed by the unmanned aerial vehicle 400 according to embodiments of the present disclosure will be described. The unmanned aerial vehicle 400 is configured to be capable of executing the four types of work content that are illustrated in FIG. 14.

"Smoke removal" is work for securing air by removing the smoke from the vicinity of the victim B3 at the fire site. Specifically, the unmanned aerial vehicle 400 hovers over the victim B3, draws smoke S into the middle opening portions 20 by using the air flow generated by the lift generating units 121a to 121d, and removes the smoke S via the smoke removal filters 410 placed in the middle opening portions 20 as illustrated in FIG. 12A. The air that is left after the removal of the smoke S is sent toward the victim B3 by the air flow. In this manner, the smoke S around the victim B3 can be removed and air can be secured.

"Victim transport" is work for transporting the victim B3 to the shelter from, for example, the inside of a building or the rooftop of a skyscraper as a fire site. Specifically, the unmanned aerial vehicle 400 transports the victim. B3 onto the ground while protecting the victim B3 from the landing impact by landing after falling at a low speed with the victim B3 at a high place and taking the victim B3 on the top of the deployed airbag 430 as illustrated in FIG. 12B. At this time, a plurality of the unmanned aerial vehicles 400 can be used as well. For example, the transport can be performed in a state where the airbag 430 of one of the unmanned aerial vehicles 400 is deployed and the victim B3 is supported by both the unmanned aerial vehicle 400 and the other unmanned aerial vehicle 400. In this manner, a plurality of the victims B3 can be transported at the same time. In addition, the victim B3 is transported from the fire site to a safe shelter in a state where the victim B3 is caught by the lift generating units 121a to 121d or the load receiving unit 116 or in a state where the victim B3 is fixed to the load receiving unit 116 by the fixing tool 440. Furthermore, the victim B3, such as a home care patient in need of assistance, is transported to the safe shelter from his or her residence at the fire site "Airbag operation" is work that is selected if necessary when the "victim transport" has been selected. It is to put into operation and deploy the airbag 430 so that the victim B3 can be protected from the landing impact.

"Fixing tool operation" is work that is selected if necessary when the "victim transport" has been selected. It is to fix the victim B3 who cannot be caught by the load receiving unit 116 to the unmanned aerial vehicle 400 by using the fixing tool 440.

Hereinafter, alternative or additional effects and/or advantages of the embodiments of the present disclosure will now be described.

The relief work that is executed by the unmanned aerial vehicle 400 includes at least one of the "avoidance of dangers around victim" and the "victim evacuation support". Accordingly, the unmanned aerial vehicle 400 is capable of avoiding the dangers around the victim B3 or performing evacuation support for the victim B3 in close proximity even at a place defying rescuers' approach such as the inside of a building or the rooftop of a skyscraper where a large fire has occurred to generate strong radiant heat.

Since the "avoidance of dangers around victim" includes the removal of the smoke S and securing of the air at the fire site, carbon monoxide poisoning can be prevented based on the protection of the victim B3 from the smoke Sand the evacuation support can be performed with the visibility of the victim B3 ensured.

Since the "victim evacuation support" includes the transport of the victim B3 from the disaster site, evacuation support for people who are in need of assistance and have a hard time performing evacuation on their own, such as inpatients and home care patients, can be performed by the unmanned aerial vehicle 400.

Since the unmanned aerial vehicle 400 has the airbag (shock absorbing unit) 430 as well, unmanned aerial vehicle 400 can protect the victim B3 from the landing impact during the transport of the victim. B3 from a high place onto a ground surface.

The plurality of unmanned aerial vehicles 400 is capable of executing the relief work in cooperation with each other. Accordingly, the relief work can be efficiently executed based on, for example, the simultaneous transport of the plurality of persons.

The unmanned aerial vehicle, the relief system, and the relief method according to the embodiments of the present disclosure have been described based on the embodiments and the plurality of modification examples described above. The present invention is not limited to what has been described based on the embodiments and the modifications herein and can be appropriately changed based on what is described in the scope of claims.

The relief work that is executed by the unmanned aerial vehicle is not particularly limited insofar as the relief work can be executed by the unmanned aerial vehicle. For example, the relief work may be work for removing rubble resulting from collapse during a disaster, work for transporting relief supplies, assistance work for senior citizens and disabled persons at evacuation facilities and so on, and complex combinations between each of those types of work and the relief work related to the embodiments aforementioned, too.

The work that can be executed by the unmanned aerial vehicle in the normal mode is not limited to the medical support work insofar as the medical support work is to support the user's work. For example, the medical support work may be monitoring work for performing constant monitoring from the sky for an early discovery of a disaster site such as a fire site.

Transmission of a transmission signal to the unmanned aerial vehicle may not be performed based on the use of the information terminal device. For example, an instruction may be directly carried out via the input IF (such as an operation switch and a touch screen) that is disposed in the unmanned aerial vehicle or the transmission command may be transmitted by the use of a dedicated controller. A data transmitting and receiving unit (slot) or the like that allows data transmission and reception to and from a storage medium such as a nonvolatile memory card can also be disposed in the unmanned aerial vehicle. In addition, various types of the relief work may be executed by the unmanned aerial vehicle being used alone without a network including the management server and the like being established.

REFERENCE SIGNS LIST

1 Relief system
100, 400 Unmanned aerial vehicle
110 Main body portion
111 Treatment unit
112 Display unit
113 Speaker
114 Microphone
115 Operation button
116 Load receiving unit
117 Imaging unit
120 Upper housing
121a, 121b, 121c, 121d Lift generating unit
130 Control unit
190 Transmitting and receiving unit (receiving unit)
200 Information terminal device
230 Control unit
231 Application execution unit
240 Output IF
280 Input IF
290 Transmitting and receiving unit
300 Management server
410 Smoke removal filter
420 Placement portion
430 Airbag (shock absorbing unit)
440 Fixing tool
A2 User
B3 Victim (relief recipient)

What is claimed is:

1. An unmanned aerial vehicle capable of performing autonomous flight, the unmanned aerial vehicle comprising:
   a receiving unit receiving an input of relief work from a user;
   a bioinformation measuring instrument that measures bioinformation of a relief recipient;
   an emergency treatment device that performs a medical treatment on the relief recipient;
   a control unit controlling execution of the relief work based on content of the input received by the receiving unit, wherein the execution of the relief work includes the unmanned aerial vehicle navigating to a site where the relief recipient is located, determining that the treatment of the relief recipient is required based on the bioinformation measured, and automatically performing the medical treatment on the relief recipient using the emergency treatment device without assistance from any person in proximity to the relief recipient at the site.

2. The unmanned aerial vehicle according to claim 1, which is configured to be capable of selectively switching between a normal mode and an emergency mode, the normal mode being a standby state where no work is executed or an operating state where task support work for supporting the user's work is performed and the emergency mode being an operating state where the relief work is performed.

3. The unmanned aerial vehicle according to claim 2, wherein the relief work includes at least one of confirmation of a state of the relief recipient, avoidance of a danger around the relief recipient, and evacuation support for the relief recipient.

4. The unmanned aerial vehicle according to claim 3, wherein the confirmation of the state of the relief recipient includes a bioinformation measurement executed simultaneously with the medical treatment, and wherein automatically performing the medical treatment on the relief recipient includes at least one of cardioversion and cardiopulmonary resuscitation.

5. The unmanned aerial vehicle according to claim 3, wherein the avoidance of the danger around the relief recipient includes smoke removal and securing of air at the site.

6. The unmanned aerial vehicle according to claim 3, wherein the evacuation support for the relief recipient includes transport of the relief recipient from the site.

7. The unmanned aerial vehicle according to claim 6, further comprising a shock absorbing unit absorbing a landing impact of the unmanned aerial vehicle upon impacting a ground surface during the transport of the relief recipient from the site.

8. The unmanned aerial vehicle according to claim 7, wherein the unmanned aerial vehicle is part of a plurality of unmanned aerial vehicles, and wherein the plurality of unmanned aerial vehicles execute the relief work in cooperation with each other.

9. A relief method for performing relief work by using an unmanned aerial vehicle capable of performing autonomous flight, the relief method comprising:
   a receiving step of receiving processing content from a user via a receiving unit of the unmanned aerial vehicle; and
   a control step of controlling the execution of the relief work following the processing content by using a control unit of the unmanned aerial vehicle, wherein controlling the execution of the relief work comprises:
      navigating the unmanned aerial vehicle to a site where a relief recipient is located;
      measuring, by a bioinformation measuring instrument associated with the unmanned aerial vehicle, bioinformation of the relief recipient at the site;
      determining that medical treatment of the relief recipient is required based on the bioinformation measured; and
      performing, automatically by an emergency treatment device associated with the unmanned aerial vehicle, the medical treatment on the relief recipient without assistance from any person in proximity to the relief recipient at the site.

10. The relief method according to claim 9, wherein the relief work includes at least one of confirmation of a state of the relief recipient, avoidance of a danger around the relief recipient, and evacuation support for the relief recipient.

11. The relief method according to claim 10, wherein the confirmation of the state of the relief recipient includes a bioinformation measurement executed simultaneously with automatically performing the medical treatment, and wherein automatically performing the medical treatment on the relief recipient includes at least one of cardioversion and cardiopulmonary resuscitation.

12. The relief method according to claim 10, wherein the avoidance of the danger around the relief recipient includes smoke removal and securing of air at the site.

13. The relief method according to claim 10, wherein the evacuation support for the relief recipient includes transport of the relief recipient from the site.

14. The relief method according to claim 13, further comprising:
   absorbing, via a shock absorbing unit associated with the unmanned aerial vehicle, a landing impact of the unmanned aerial vehicle upon impacting a ground surface during the transport of the relief recipient from the site.

15. The relief method according to claim 14, wherein the unmanned aerial vehicle is part of a plurality of unmanned aerial vehicles, and wherein the plurality of unmanned aerial vehicles execute the relief work in cooperation with each other.

16. An information terminal device capable of controlling an unmanned aerial vehicle that is capable of autonomous flight, the information terminal device comprising:
   an input interface to send an input of relief support work from a user;
   a transmitting and receiving unit in communication with the input interface, the transmitting and receiving unit to transmit the input of relief support work to the unmanned aerial vehicle; and
   a control unit in communication with the input interface and the transmitting and receiving unit, the control unit to control the execution of the relief support work based on content of the input received by the receiving unit, wherein controlling the execution of the relief support work comprises:
   navigating the unmanned aerial vehicle to a site where a relief recipient is located;
   measuring, by a bioinformation measuring instrument associated with the unmanned aerial vehicle, bioinformation of the relief recipient at the site;
   determining that medical treatment of the relief recipient is required based on the bioinformation measured; and
   performing, automatically by an emergency treatment device associated with the unmanned aerial vehicle, the medical treatment on the relief recipient without assistance from any person in proximity to the relief recipient at the site.

17. The information terminal device according to claim 16, wherein the relief support work includes at least one of confirmation of a state of the relief recipient, avoidance of a danger around the relief recipient, and evacuation support for the relief recipient.

18. The information terminal device according to claim 17, wherein the confirmation of the state of the relief recipient includes a bioinformation measurement executed simultaneously with automatically performing the medical treatment, and wherein automatically performing the medical treatment on the relief recipient includes at least one of cardioversion and cardiopulmonary resuscitation.

19. The information terminal device according to claim 17, wherein the avoidance of the danger around the relief recipient includes smoke removal and securing of air at the site.

20. The information terminal device according to claim 17, wherein the evacuation support for the relief recipient includes transport of the relief recipient from the site.

* * * * *